(12) United States Patent
Schirrmacher et al.

(10) Patent No.: US 7,896,910 B2
(45) Date of Patent: Mar. 1, 2011

(54) MODULAR APPARATUS FOR THERAPY OF AN ANIMATE BODY

(75) Inventors: Tamara Lynn Schirrmacher, Alameda, CA (US); David Selby Maltz, San Francisco, CA (US)

(73) Assignee: CoolSystems, Inc., Alameda, CA (US)

( * ) Notice: Subject to any disclaimer, the term of this patent is extended or adjusted under 35 U.S.C. 154(b) by 1852 days.

(21) Appl. No.: 10/848,097

(22) Filed: May 17, 2004

(65) Prior Publication Data

US 2005/0256556 A1 Nov. 17, 2005

(51) Int. Cl.
*A61F 7/00* (2006.01)
(52) U.S. Cl. .......................... 607/104; 607/105
(58) Field of Classification Search .............. 607/96, 607/104, 108–112

See application file for complete search history.

(56) References Cited

U.S. PATENT DOCUMENTS

| | | |
|---|---|---|
| 1,958,899 A | 5/1934 | MacAdams |
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 3,261,042 A | 7/1966 | Baker |
| 3,320,682 A | 5/1967 | Sliman |
| 3,354,898 A | 11/1967 | Barnes |
| 3,561,435 A | 2/1971 | Nicholson |
| 3,738,367 A | 6/1973 | Hardy |
| 3,744,555 A | 7/1973 | Fletcher et al. |
| 3,830,676 A | 8/1974 | Elkins |
| 3,871,381 A | 3/1975 | Roslonski |
| 3,901,225 A | 8/1975 | Sconce |
| 3,993,053 A | 11/1976 | Grossan |
| 4,026,299 A | 5/1977 | Sauder |
| 4,116,476 A | 9/1978 | Porter et al. |

(Continued)

FOREIGN PATENT DOCUMENTS

DE 3343664 3/1985

(Continued)

OTHER PUBLICATIONS

Elkins, U.S. Appl. No. 09/173,637 entitled "Compliant heat exchange splint and control unit," filed Oct. 16, 1998.

(Continued)

*Primary Examiner* — Roy D Gibson
(74) *Attorney, Agent, or Firm* — Shay Glenn LLP

(57) ABSTRACT

Modular therapy apparatus for treatment of at least a portion of an animate body comprises a first modular member and a second modular member. The first modular member comprises a heat transfer device adapted to transfer heat between the device and the at least a portion of an animate body. The second modular member forms a pouch having a perimeter and is adapted to receive the first modular member. The second modular member comprises a front side and a back side. The front side has a hook portion, which forms the hook portion of a hook and loop fastener. The back side has a loop portion, which forms the loop portion of the hook and loop fastener. The second modular member can be wrapped around the at least a portion of an animate body and the hook and loop portions fastened to one another to secure the second modular member with the first modular member positioned therein to the at least a portion of the animate body.

8 Claims, 18 Drawing Sheets

U.S. PATENT DOCUMENTS

| Patent No. | | Date | Inventor | Ref |
|---|---|---|---|---|
| 4,118,946 A | | 10/1978 | Tubin | |
| 4,147,921 A | | 4/1979 | Walter et al. | |
| 4,149,529 A | | 4/1979 | Copeland et al. | |
| 4,149,541 A | | 4/1979 | Gammons et al. | |
| 4,194,247 A | | 3/1980 | Melander | |
| 4,338,944 A | * | 7/1982 | Arkans | 607/104 |
| 4,412,648 A | | 11/1983 | Ford et al. | |
| 4,436,125 A | | 3/1984 | Blenkush | |
| 4,471,759 A | | 9/1984 | Anderson et al. | |
| 4,478,436 A | | 10/1984 | Hashimoto | |
| 4,547,906 A | | 10/1985 | Nishida | |
| 4,597,384 A | | 7/1986 | Whitney | |
| 4,678,027 A | | 7/1987 | Shirey et al. | |
| 4,691,762 A | | 9/1987 | Elkins et al. | |
| 4,718,429 A | | 1/1988 | Smidt | |
| 4,738,119 A | | 4/1988 | Zafred | |
| 4,753,268 A | | 6/1988 | Palau | |
| 4,765,338 A | * | 8/1988 | Turner et al. | 607/110 |
| 4,844,072 A | | 7/1989 | French et al. | |
| 4,884,304 A | | 12/1989 | Elkins | |
| 4,925,603 A | | 5/1990 | Nambu | |
| 4,955,435 A | | 9/1990 | Shuster et al. | |
| 4,964,282 A | | 10/1990 | Wagner | |
| 4,976,262 A | * | 12/1990 | Palmacci | 607/108 |
| 5,002,270 A | | 3/1991 | Shine | |
| 5,014,695 A | | 5/1991 | Benak et al. | |
| 5,022,109 A | | 6/1991 | Pekar | |
| 5,033,136 A | | 7/1991 | Elkins | |
| 5,052,725 A | | 10/1991 | Meyer et al. | |
| 5,072,875 A | | 12/1991 | Zacoi | |
| 5,074,285 A | | 12/1991 | Wright | |
| 5,076,068 A | | 12/1991 | Mikhail | |
| 5,080,089 A | | 1/1992 | Mason et al. | |
| 5,080,166 A | | 1/1992 | Haugeneder | |
| 5,086,771 A | | 2/1992 | Molloy | |
| 5,097,829 A | | 3/1992 | Quisenberry | |
| 5,104,158 A | | 4/1992 | Meyer et al. | |
| 5,113,877 A | | 5/1992 | Johnson, Jr. et al. | |
| 5,163,425 A | | 11/1992 | Nambu et al. | |
| 5,172,689 A | | 12/1992 | Wright | |
| 5,201,552 A | | 4/1993 | Hohmann et al. | |
| 5,230,335 A | | 7/1993 | Johnson, Jr. et al. | |
| 5,241,951 A | | 9/1993 | Mason et al. | |
| 5,243,706 A | | 9/1993 | Frim et al. | |
| 5,269,369 A | | 12/1993 | Faghri | |
| 5,294,156 A | | 3/1994 | Kumazaki et al. | |
| 5,314,455 A | | 5/1994 | Johnson, Jr. et al. | |
| 5,316,547 A | | 5/1994 | Gildersleeve | |
| 5,353,605 A | | 10/1994 | Naaman | |
| 5,354,101 A | | 10/1994 | Anderson, Jr. | |
| 5,354,103 A | | 10/1994 | Torrence et al. | |
| 5,383,689 A | | 1/1995 | Wolfe, Sr. | |
| RE34,883 E | | 3/1995 | Grim | |
| 5,395,399 A | * | 3/1995 | Rosenwald | 607/108 |
| 5,407,421 A | | 4/1995 | Goldsmith | |
| 5,411,541 A | * | 5/1995 | Bell et al. | 607/104 |
| 5,415,625 A | | 5/1995 | Cassford et al. | |
| 5,417,720 A | | 5/1995 | Mason | |
| 5,427,577 A | | 6/1995 | Picchietti et al. | |
| 5,441,533 A | | 8/1995 | Johnson et al. | |
| 5,449,379 A | | 9/1995 | Hadtke | |
| 5,451,201 A | | 9/1995 | Prengler | |
| 5,466,250 A | | 11/1995 | Johnson, Jr. et al. | |
| 5,470,353 A | | 11/1995 | Jensen | |
| 5,476,489 A | | 12/1995 | Koewler | |
| 5,494,074 A | | 2/1996 | Ramacier, Jr. et al. | |
| 5,496,358 A | | 3/1996 | Rosenwald | |
| 5,520,622 A | | 5/1996 | Bastyr et al. | |
| 5,524,293 A | | 6/1996 | Kung | |
| 5,527,268 A | | 6/1996 | Gildersleeve et al. | |
| 5,533,354 A | | 7/1996 | Pirkle | |
| 5,539,934 A | | 7/1996 | Ponder | |
| 5,554,119 A | * | 9/1996 | Harrison et al. | 604/103.01 |
| 5,556,138 A | | 9/1996 | Nakajima et al. | |
| 5,564,124 A | | 10/1996 | Elsherif et al. | |
| 5,630,328 A | | 5/1997 | Hise et al. | |
| 5,645,671 A | | 7/1997 | Tillinghast | |
| 5,683,118 A | | 11/1997 | Slocum | |
| 5,792,216 A | | 8/1998 | Kappel | |
| 5,833,638 A | | 11/1998 | Nelson | |
| 5,865,841 A | | 2/1999 | Kolen et al. | |
| 5,868,690 A | | 2/1999 | Eischen, Sr. | |
| 5,913,885 A | | 6/1999 | Klatz et al. | |
| 5,920,934 A | | 7/1999 | Hannagan et al. | |
| 5,967,225 A | | 10/1999 | Jenkins | |
| 5,968,072 A | | 10/1999 | Hite et al. | |
| 5,970,519 A | | 10/1999 | Weber | |
| 5,980,561 A | | 11/1999 | Kolen et al. | |
| 5,984,885 A | | 11/1999 | Gaylord, Jr. et al. | |
| 5,989,285 A | | 11/1999 | DeVilbiss et al. | |
| 5,992,459 A | | 11/1999 | Sugita et al. | |
| 6,030,412 A | | 2/2000 | Klatz et al. | |
| 6,036,107 A | | 3/2000 | Aspen et al. | |
| 6,053,169 A | | 4/2000 | Hunt | |
| 6,083,256 A | * | 7/2000 | Der Ovanesian | 607/114 |
| 6,105,382 A | | 8/2000 | Reason | |
| 6,109,338 A | | 8/2000 | Butzer | |
| 6,117,164 A | | 9/2000 | Gildersleeve et al. | |
| 6,146,413 A | | 11/2000 | Harman | |
| 6,156,059 A | | 12/2000 | Olofsson | |
| 6,178,562 B1 | | 1/2001 | Elkins | |
| 6,261,314 B1 | | 7/2001 | Rich | |
| 6,306,112 B2 | | 10/2001 | Bird | |
| 6,328,276 B1 | | 12/2001 | Falch et al. | |
| 6,352,550 B1 | * | 3/2002 | Gildersleeve et al. | 607/108 |
| 6,354,635 B1 | | 3/2002 | Dyson et al. | |
| 6,361,514 B1 | | 3/2002 | Brown et al. | |
| 6,368,357 B1 | | 4/2002 | Schon et al. | |
| 6,371,976 B1 | | 4/2002 | Vrzalik et al. | |
| 6,382,678 B1 | | 5/2002 | Field et al. | |
| 6,443,498 B1 | | 9/2002 | Liao | |
| 6,547,284 B2 | | 4/2003 | Rose et al. | |
| 6,551,347 B1 | | 4/2003 | Elkins | |
| 6,551,348 B1 | | 4/2003 | Blalock et al. | |
| 6,645,232 B2 | | 11/2003 | Carson | |
| 6,695,872 B2 | | 2/2004 | Elkins | |
| 6,823,682 B1 | | 11/2004 | Jenkins et al. | |
| 6,871,878 B2 | | 3/2005 | Miros | |
| 6,926,311 B2 | | 8/2005 | Chang et al. | |
| 6,942,015 B1 | | 9/2005 | Jenkins | |
| 7,008,445 B2 | | 3/2006 | Lennox | |
| 7,107,629 B2 | | 9/2006 | Miros et al. | |
| 7,198,093 B1 | | 4/2007 | Elkins | |
| 7,306,568 B2 | * | 12/2007 | Richard | 601/15 |
| 7,490,620 B2 | | 2/2009 | Tesluk et al. | |
| 2001/0018604 A1 | | 8/2001 | Elkins | |
| 2001/0034545 A1 | | 10/2001 | Elkins | |
| 2001/0034546 A1 | | 10/2001 | Elkins | |
| 2001/0039439 A1 | | 11/2001 | Elkins et al. | |
| 2002/0019657 A1 | | 2/2002 | Elkins | |
| 2004/0167594 A1 | | 8/2004 | Elkins | |
| 2005/0143796 A1 | | 6/2005 | Augustine et al. | |
| 2005/0143797 A1 | | 6/2005 | Parish et al. | |
| 2008/0195012 A1 | | 8/2008 | Miros et al. | |
| 2009/0005841 A1 | | 1/2009 | Schirrmacher et al. | |
| 2009/0066079 A1 | | 3/2009 | Miros et al. | |

FOREIGN PATENT DOCUMENTS

| | | | |
|---|---|---|---|
| EP | 1329676 A1 | 7/2003 | |
| FR | 819022 | 10/1937 | |
| IT | 330552 | 10/1935 | |
| WO | WO92/13506 A1 | 8/1992 | |
| WO | WO92/15263 A1 | 9/1992 | |
| WO | WO94/09732 A1 | 5/1994 | |
| WO | WO96/26693 A1 | 9/1996 | |
| WO | WO98/07397 A1 | 2/1998 | |
| WO | WO99/44552 A1 | 9/1999 | |
| WO | WO00/23016 A1 | 4/2000 | |
| WO | WO00/55542 A1 | 9/2000 | |
| WO | WO00/67685 A1 | 11/2000 | |

OTHER PUBLICATIONS

Lowe et al.; U.S. Appl. No. 12/329,461 entitled "Cooling system having bypass valve to regulate fluid flow," filed Dec. 5, 2009.

Tomlinson et al.; U.S. Appl. No. 12/329,481 entitled "Therapeutic cooling and/or heating system including a thermo-conductive material," filed Dec. 5, 2009.

BioCompression Systems, Inc. (Moonachie, NJ); Product literature for Sequential Circulators; 15 pgs.

Van Eps et al.; distal limb cryotherapy for the prevention of acute laminitis; Clin Tech Equine Pract; vol. 3; pp. 64-70; 2004.

Van Eps et al.; Equine laminitis: cryotherapy reduces the severity of the acute lesion; Equine Veterinary Journal; vol. 36; No. 3; pp. 255-260; Apr. 2004.

* cited by examiner

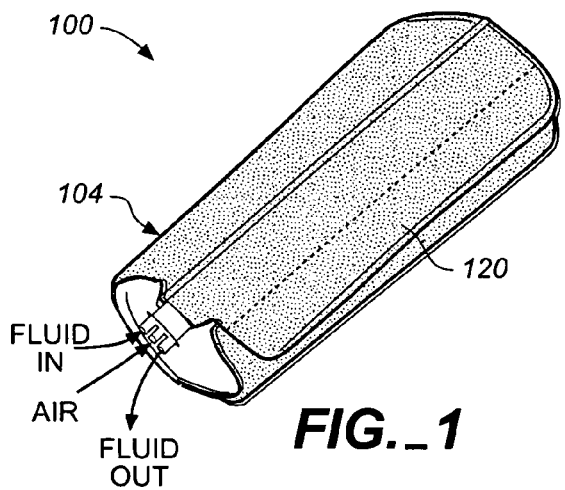
FIG._1
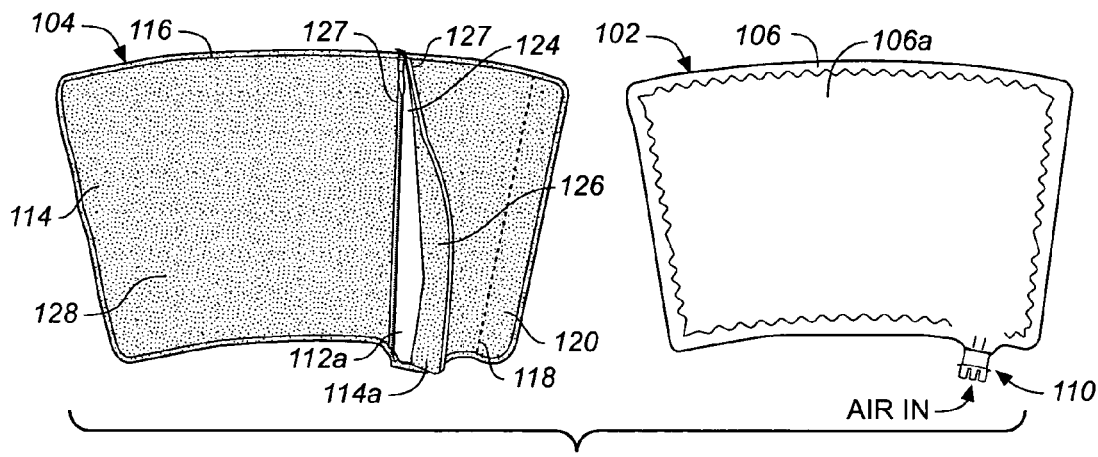
FIG._2
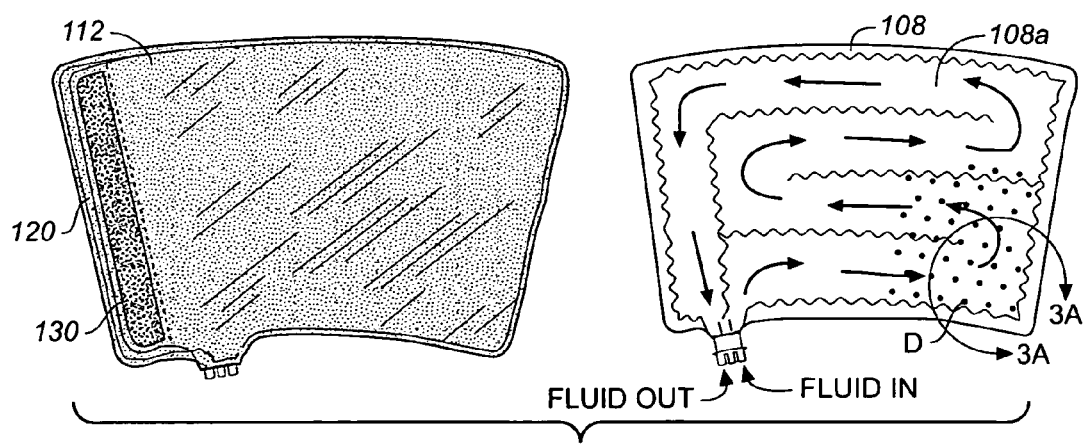
FIG._3

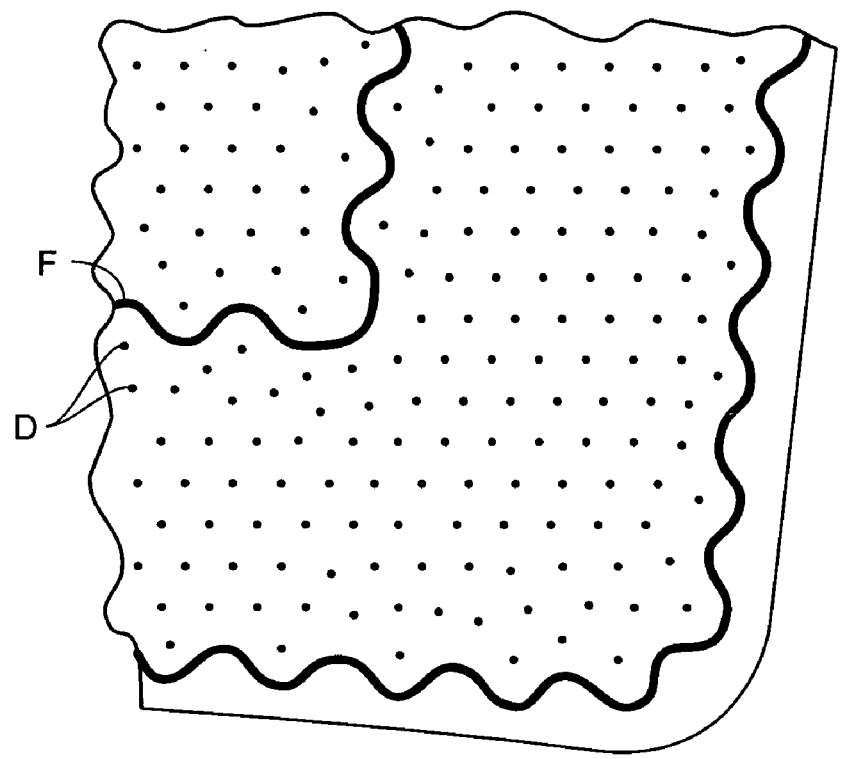
FIG._3A
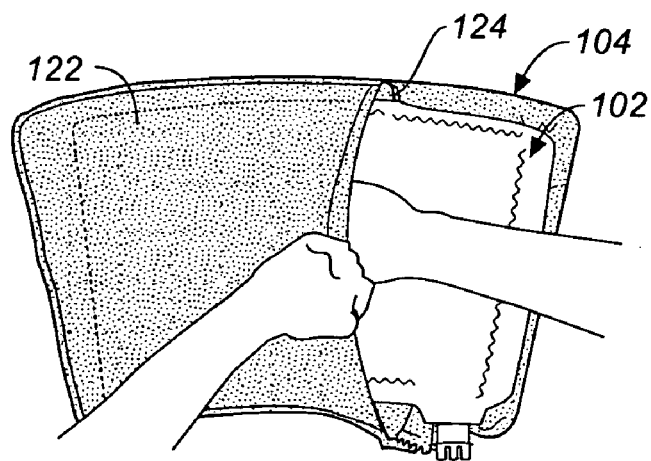
FIG._4

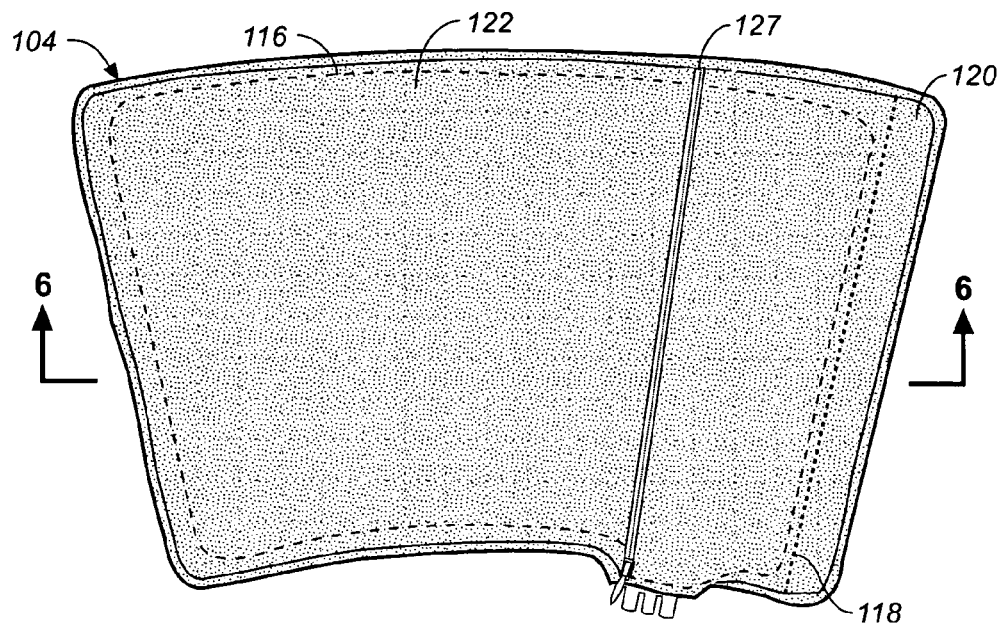
FIG._5A
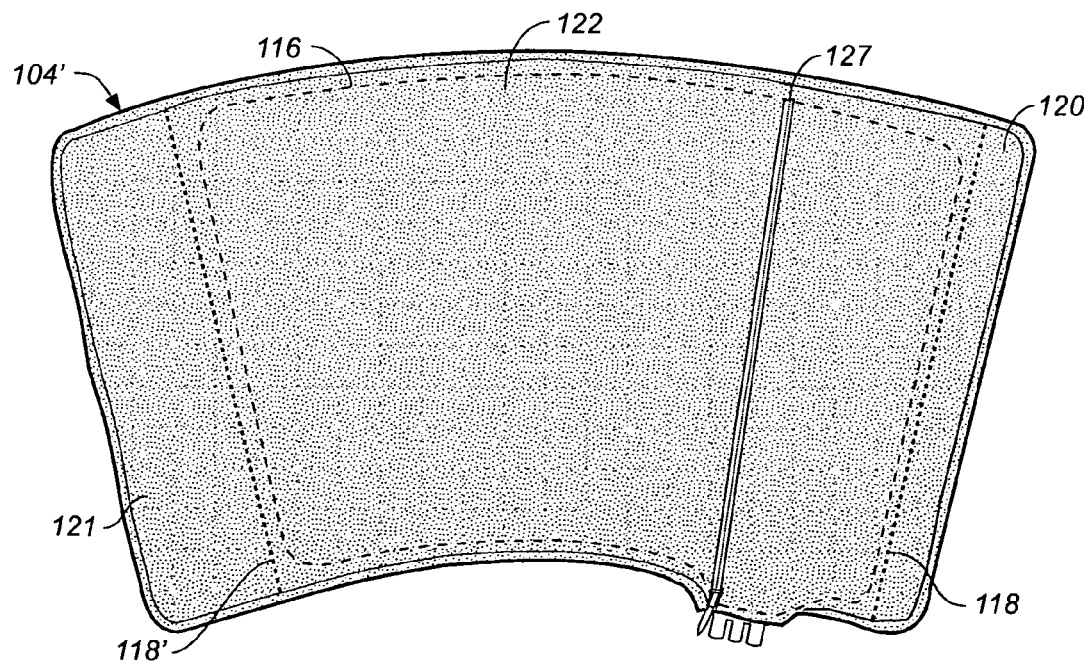
FIG._5B

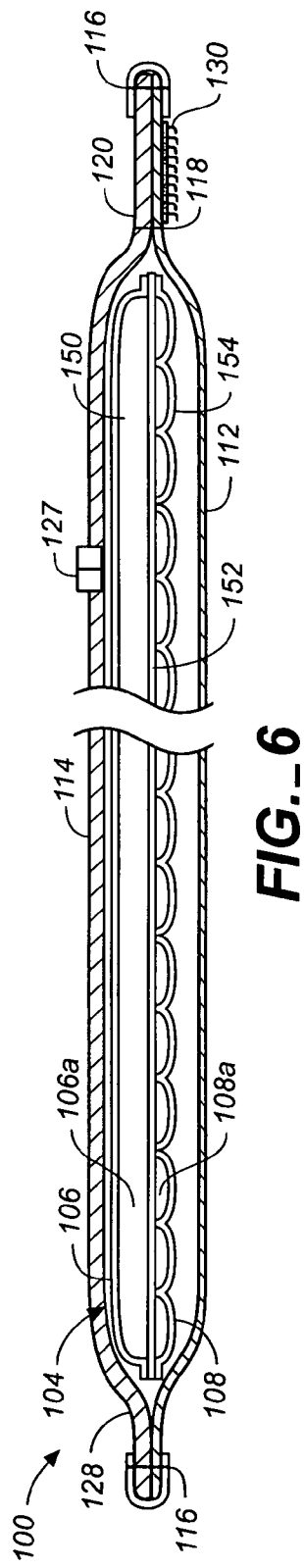
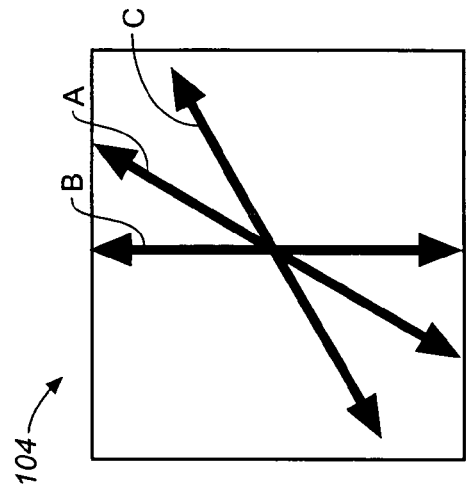
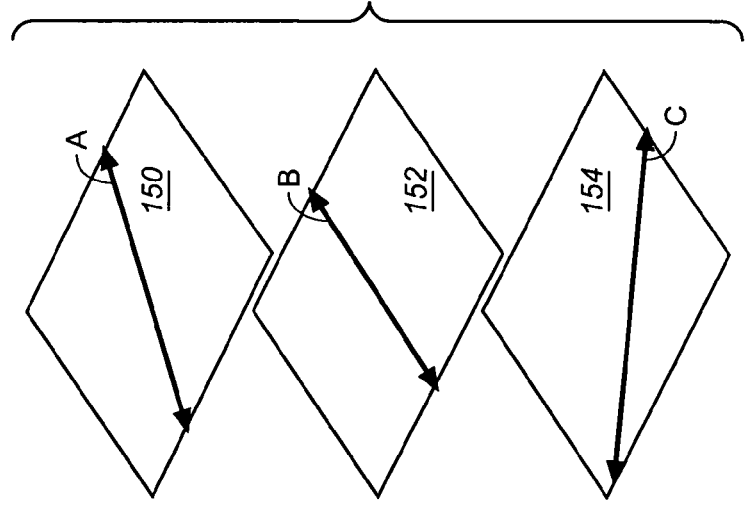
FIG._6
FIG._6B
FIG._6A

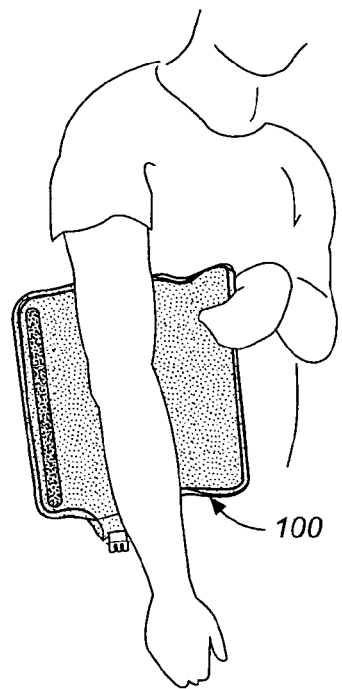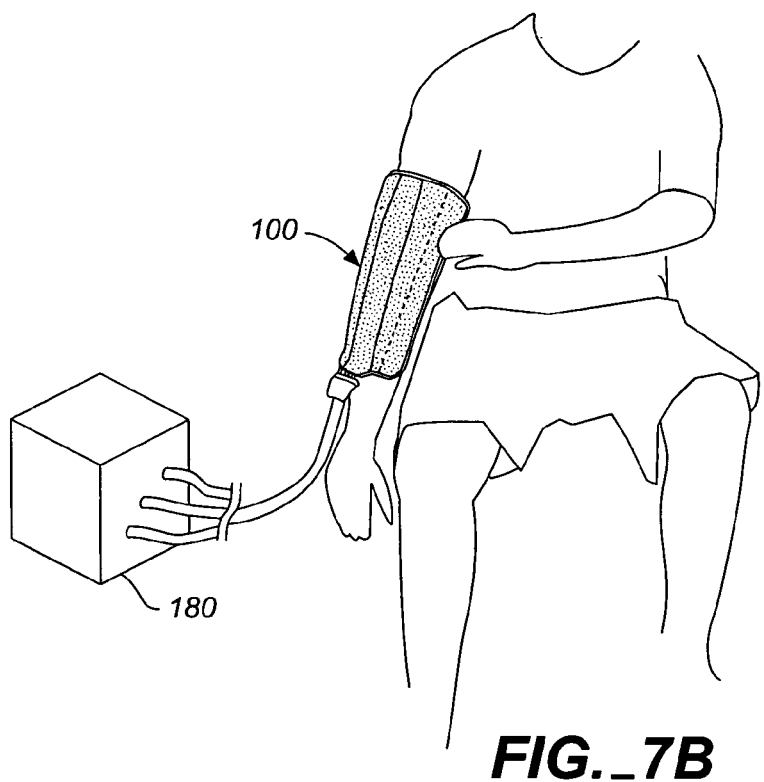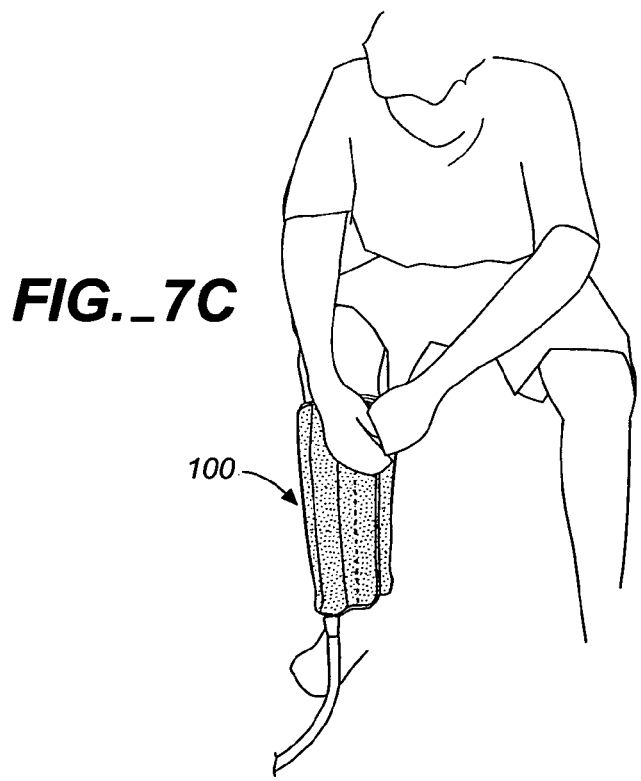
FIG._7A
FIG._7B
FIG._7C

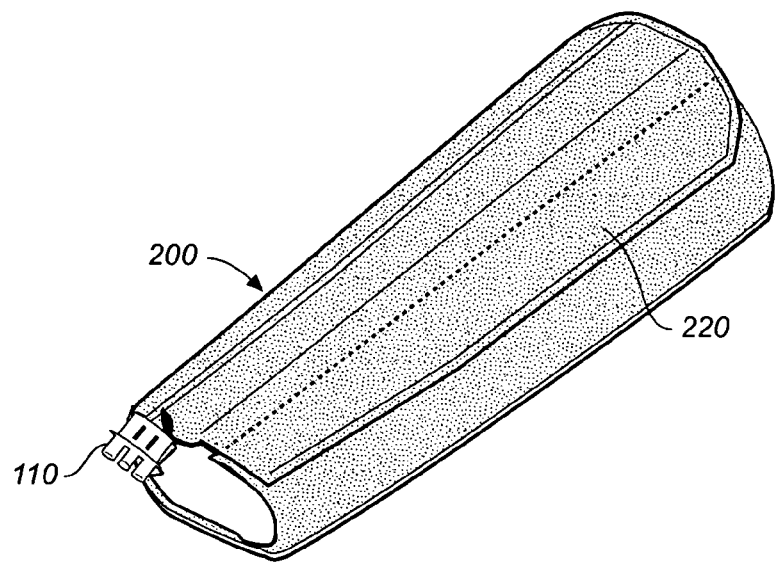
FIG._8
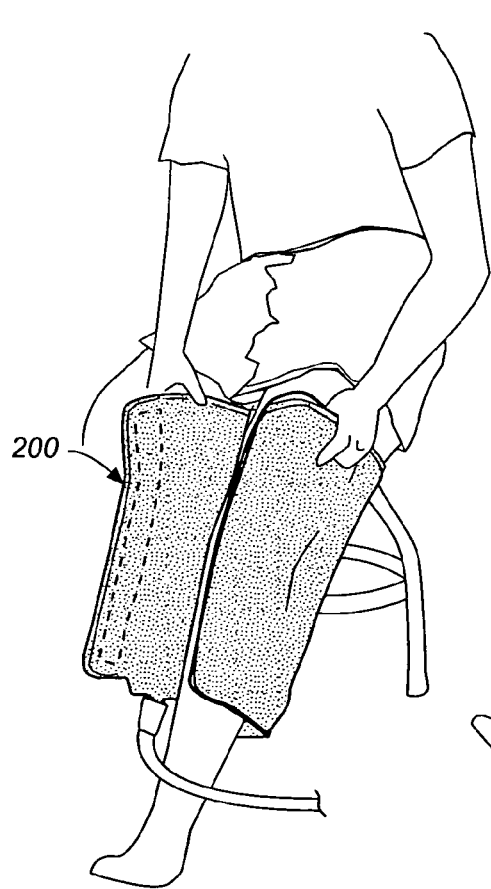
FIG._9A
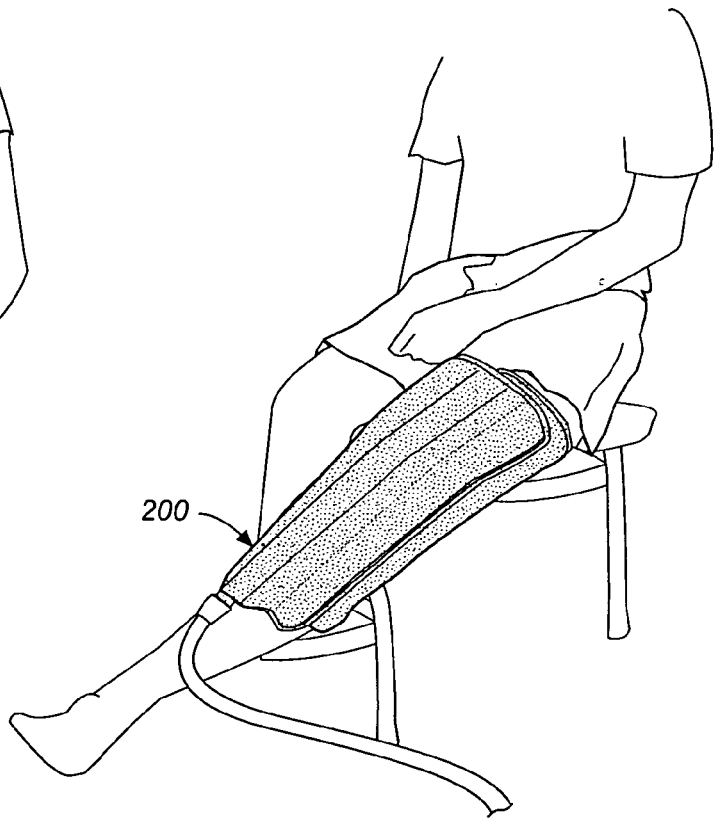
FIG._9B

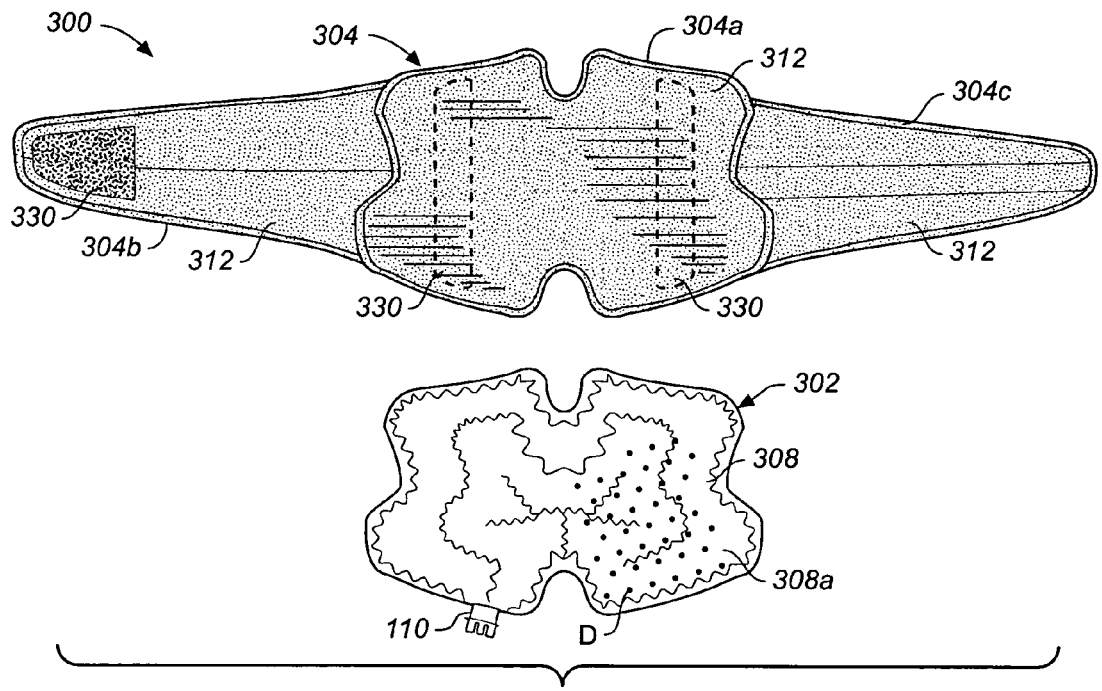
FIG._10
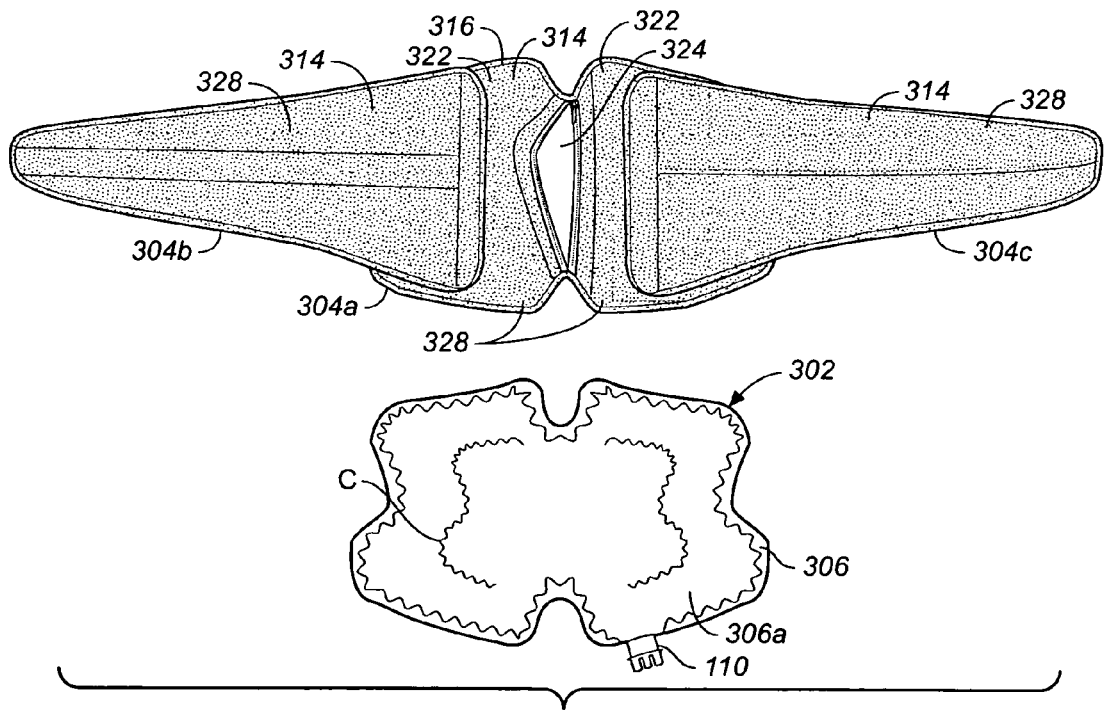
FIG._11

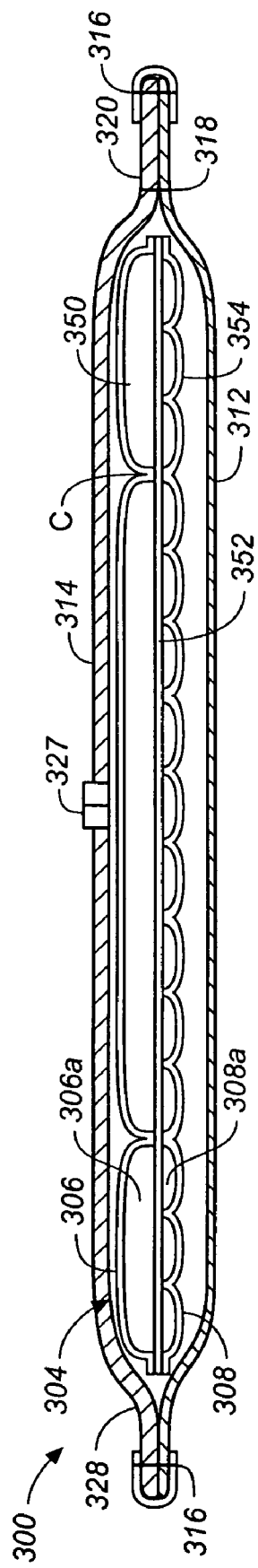
FIG._12

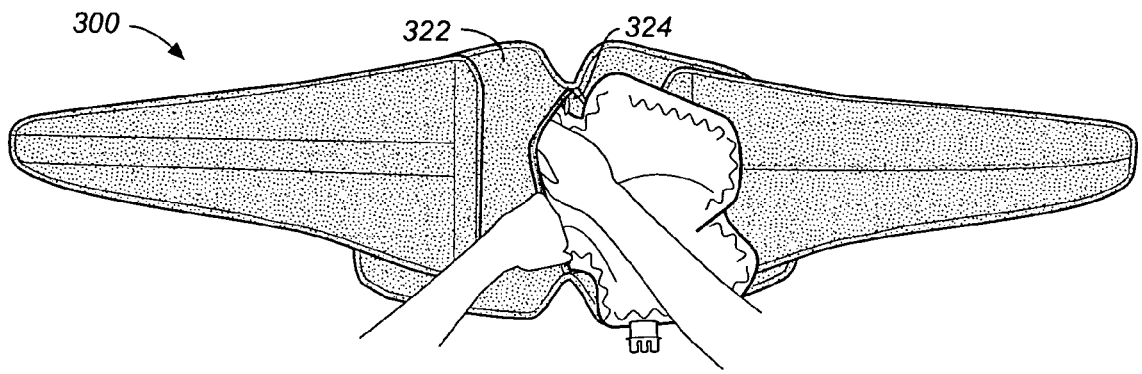
FIG._13A
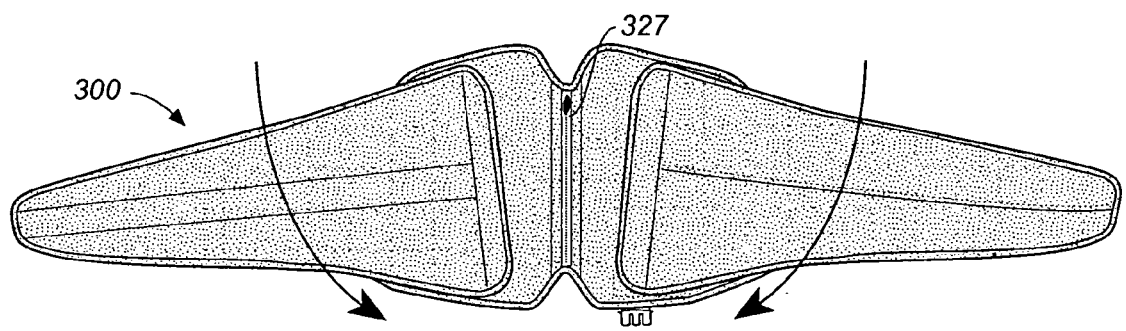
FIG._13B
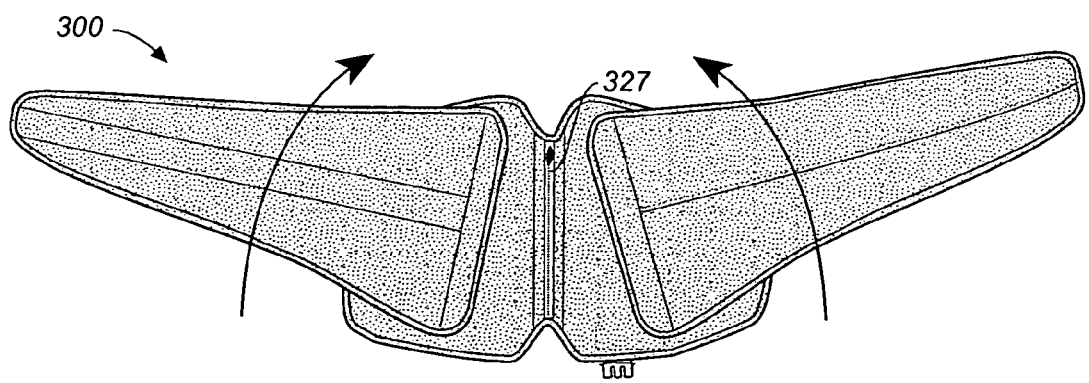
FIG._13C

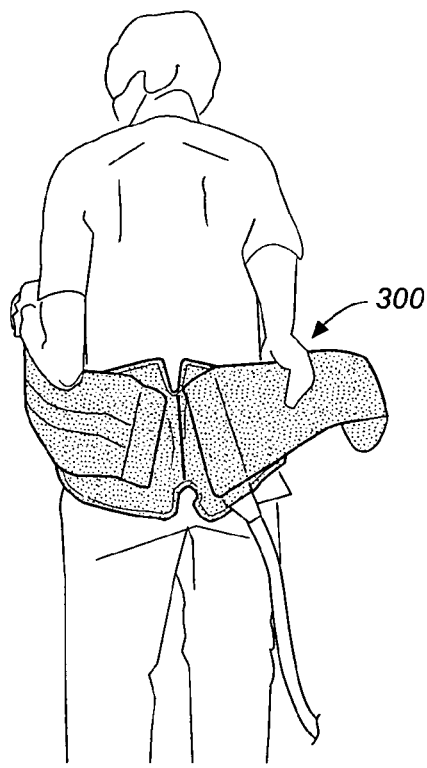
FIG._14A
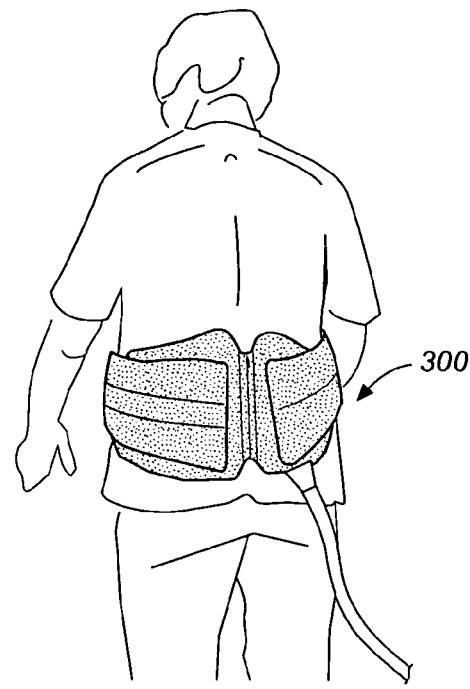
FIG._14B
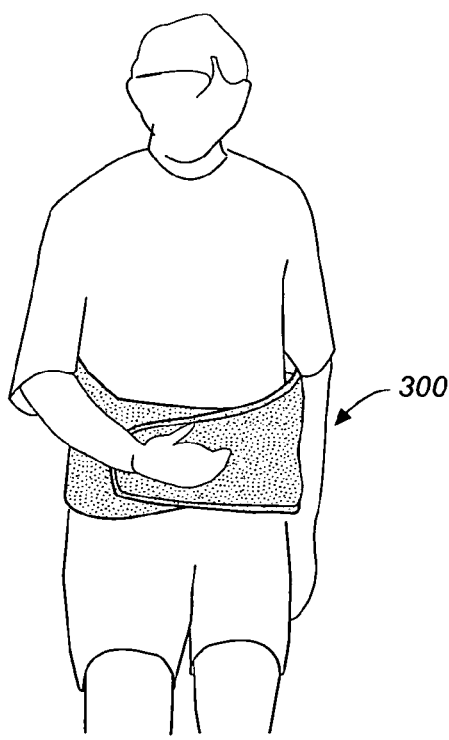
FIG._14C
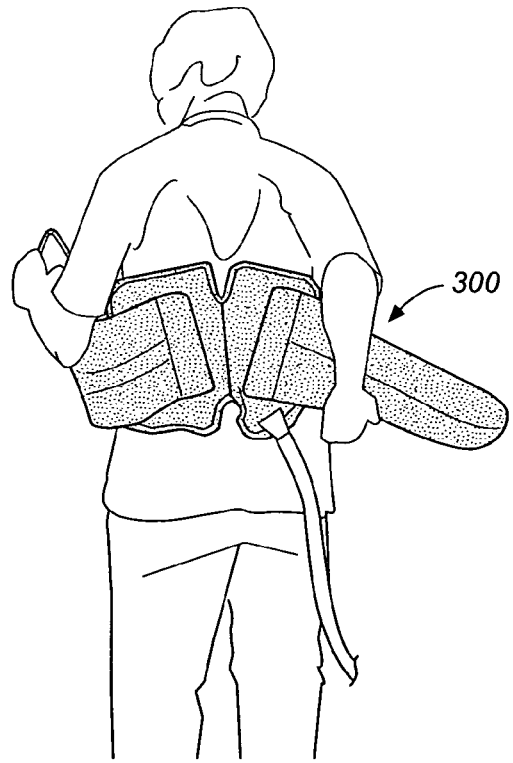
FIG._14D

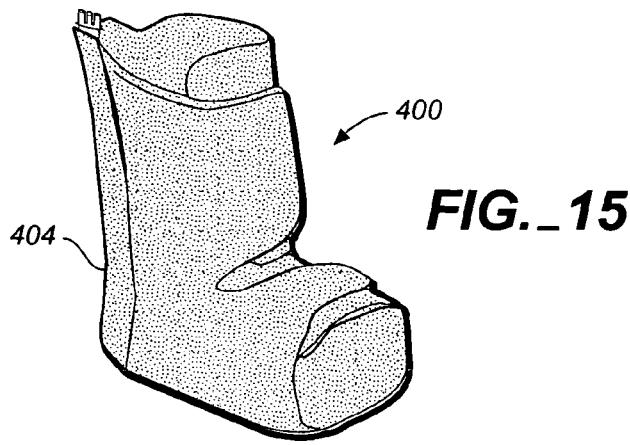
FIG._15
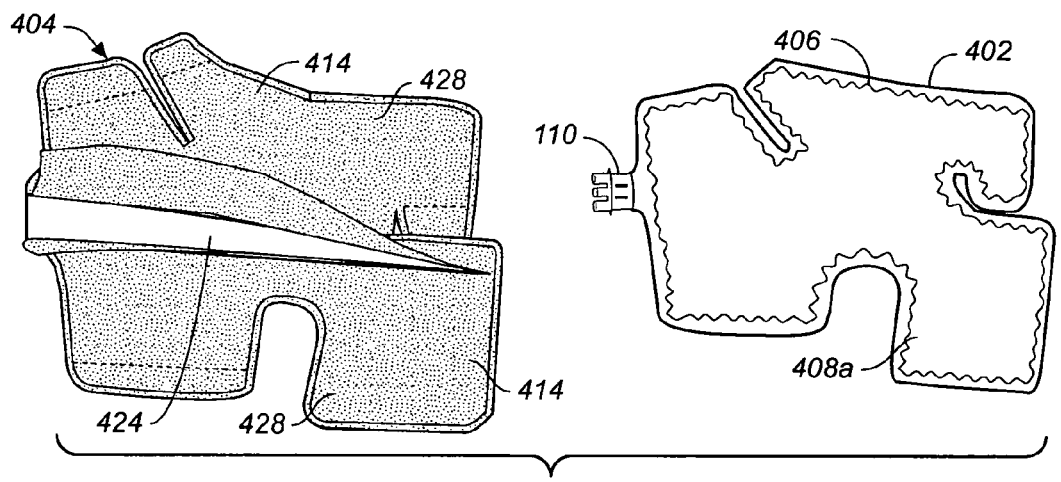
FIG._16
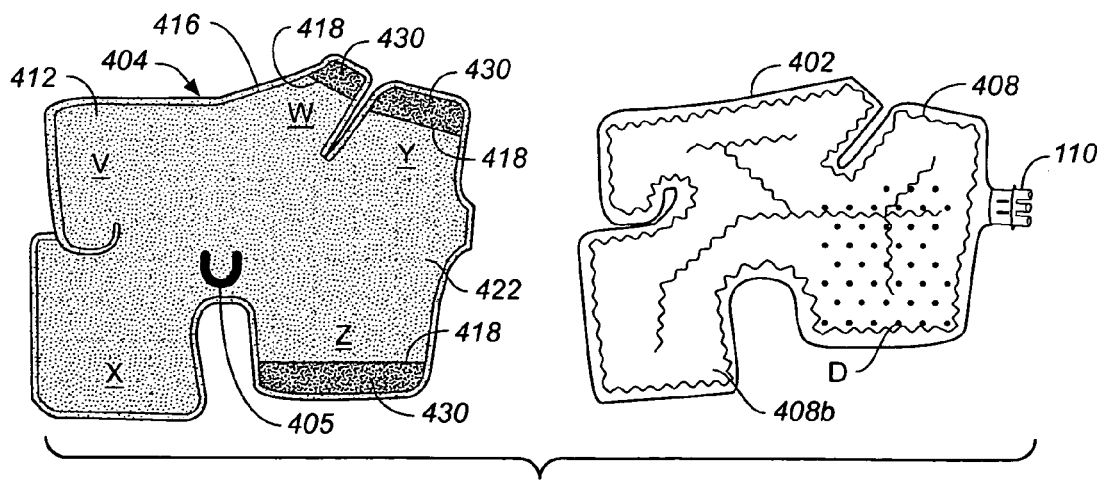
FIG._17

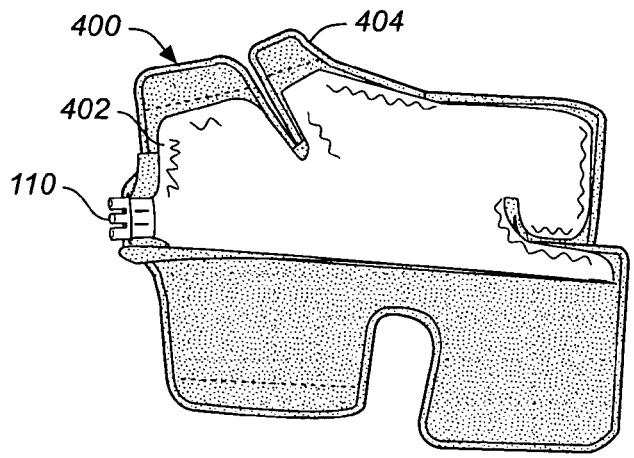
FIG._18A
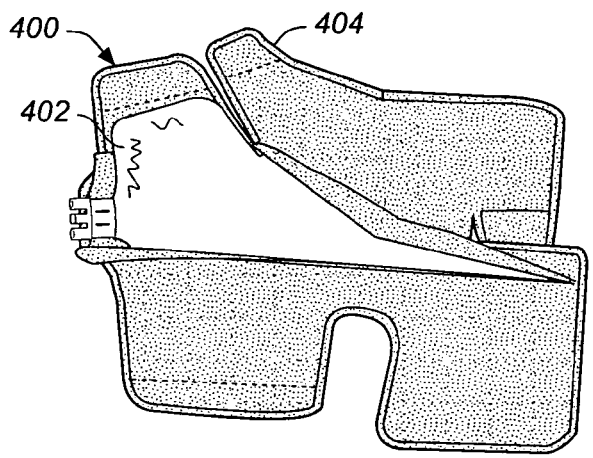
FIG._18B
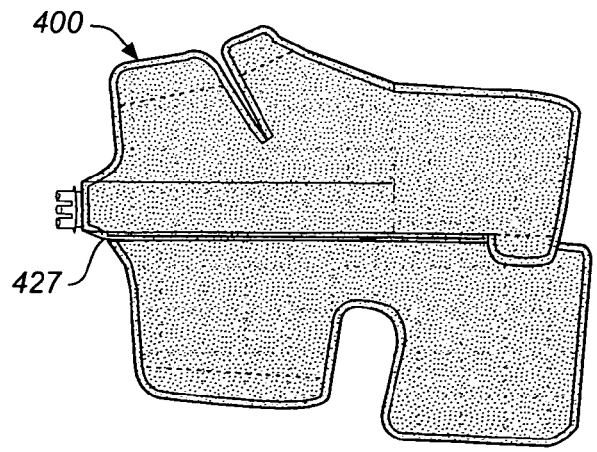
FIG._18C

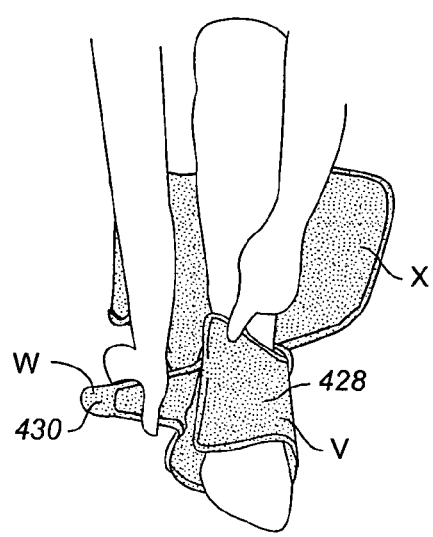
FIG._19A
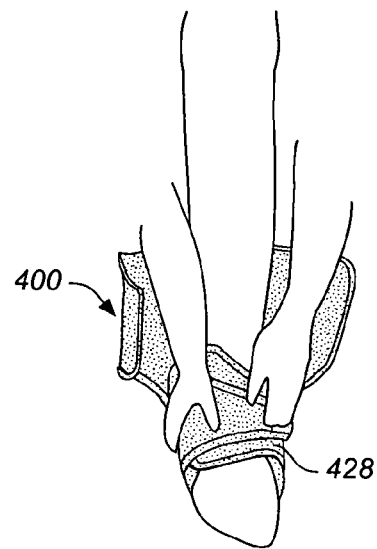
FIG._19B
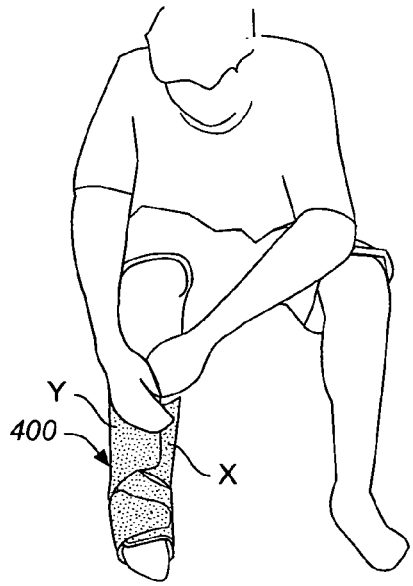
FIG._19C
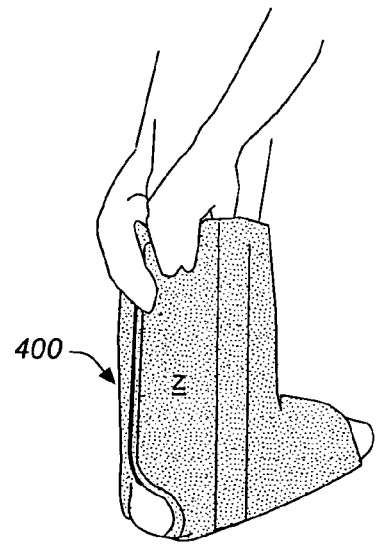
FIG._19D
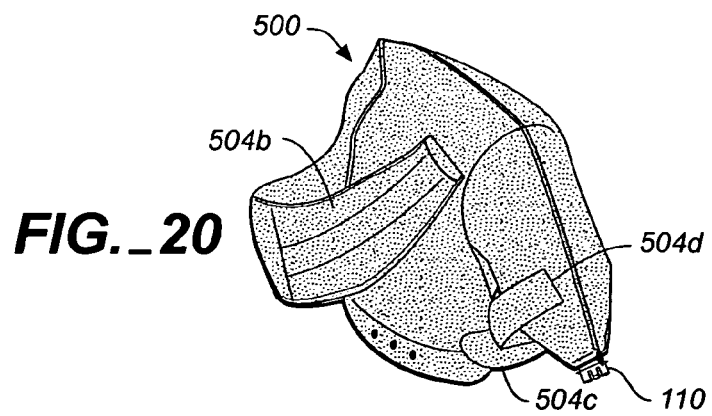
FIG._20

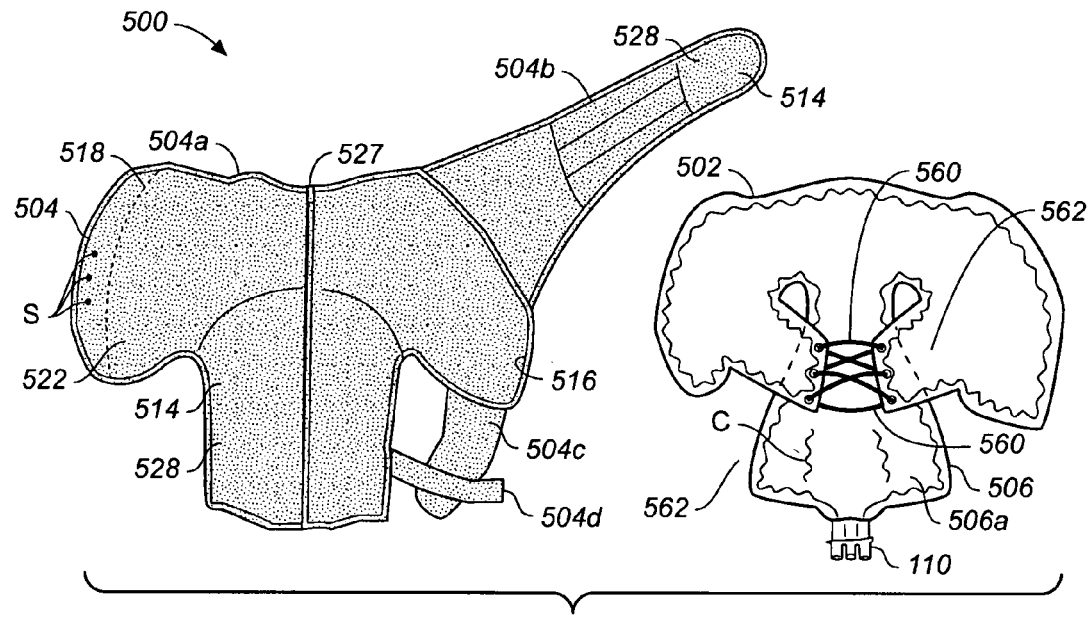
FIG._21
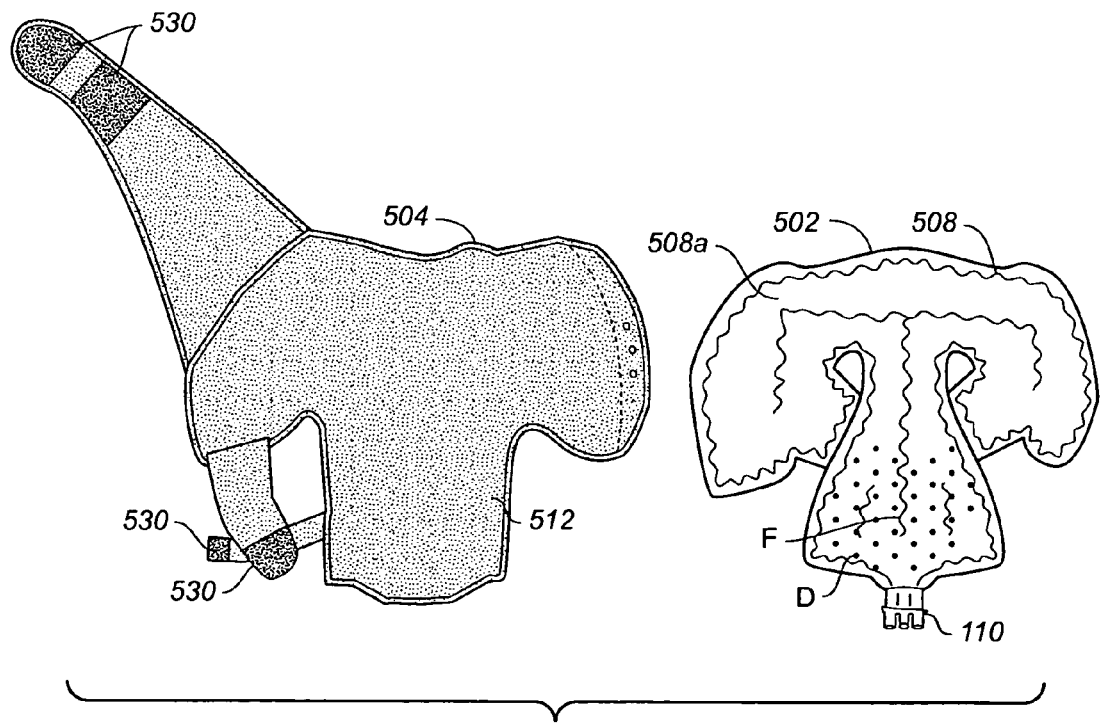
FIG._22

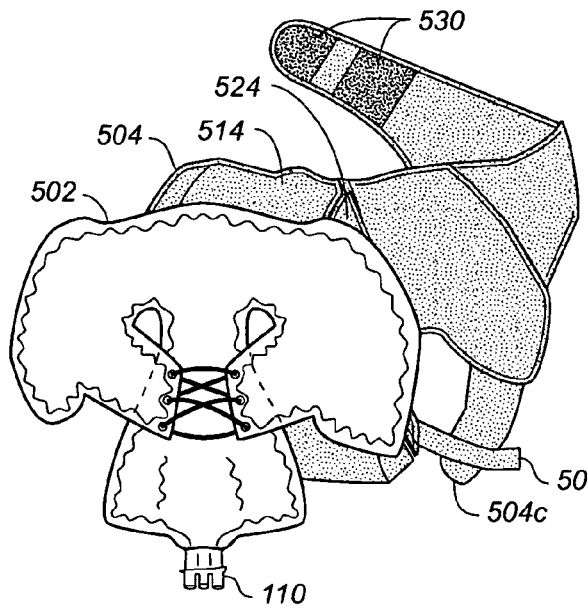
FIG._23A
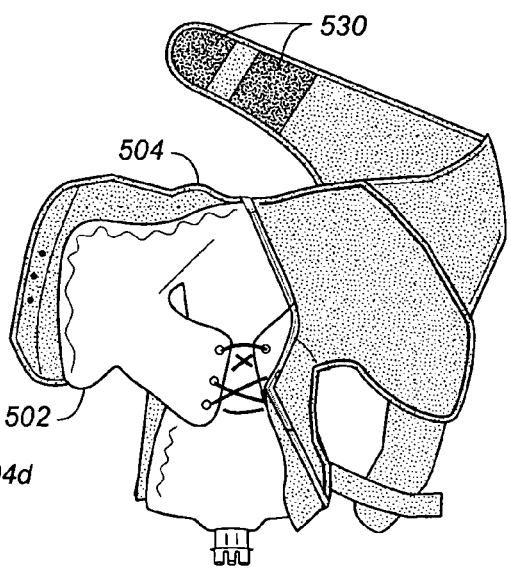
FIG._23B
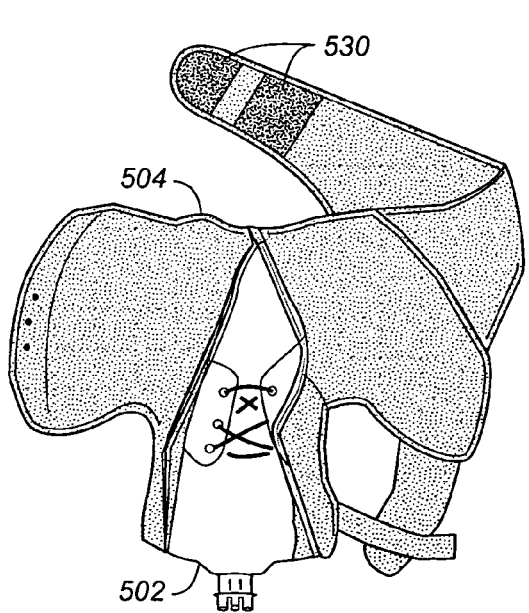
FIG._23C
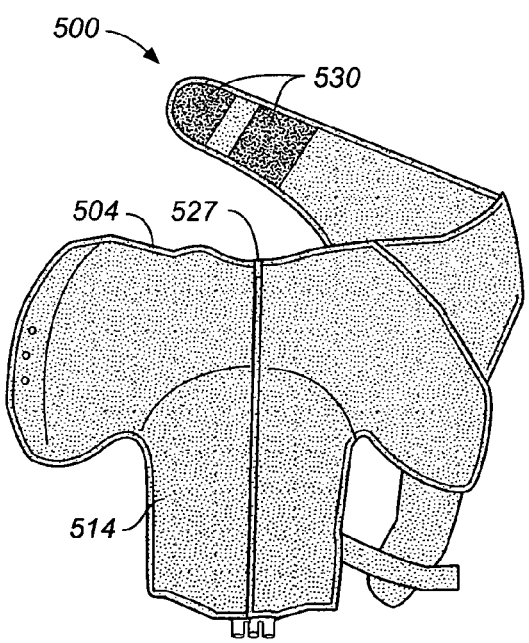
FIG._23D

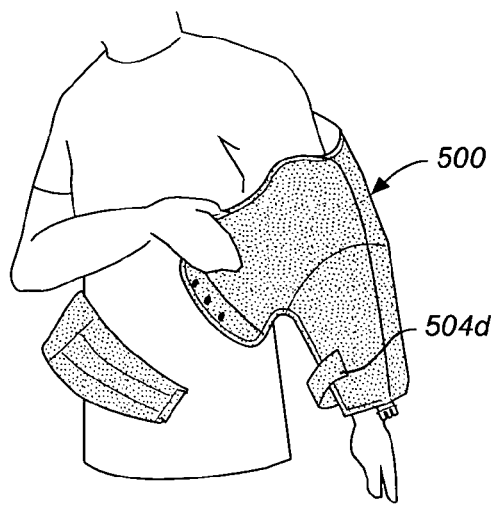
FIG._24A
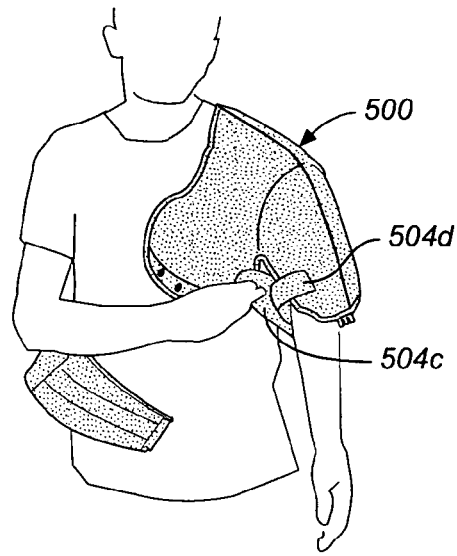
FIG._24B
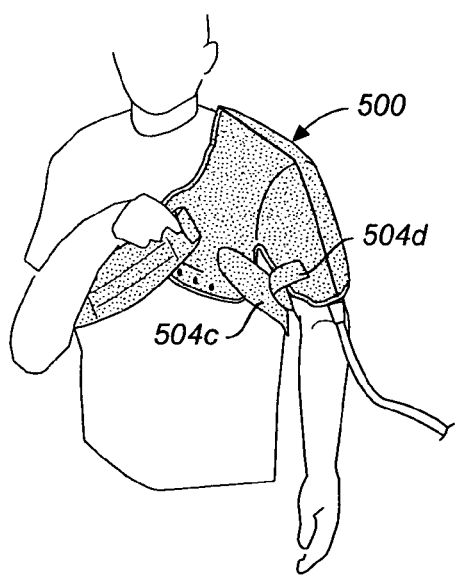
FIG._24C
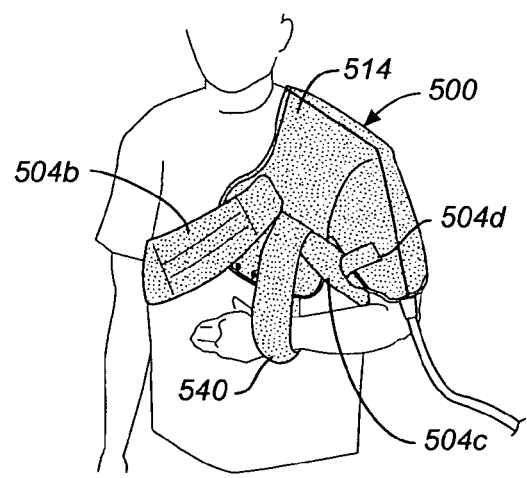
FIG._24D

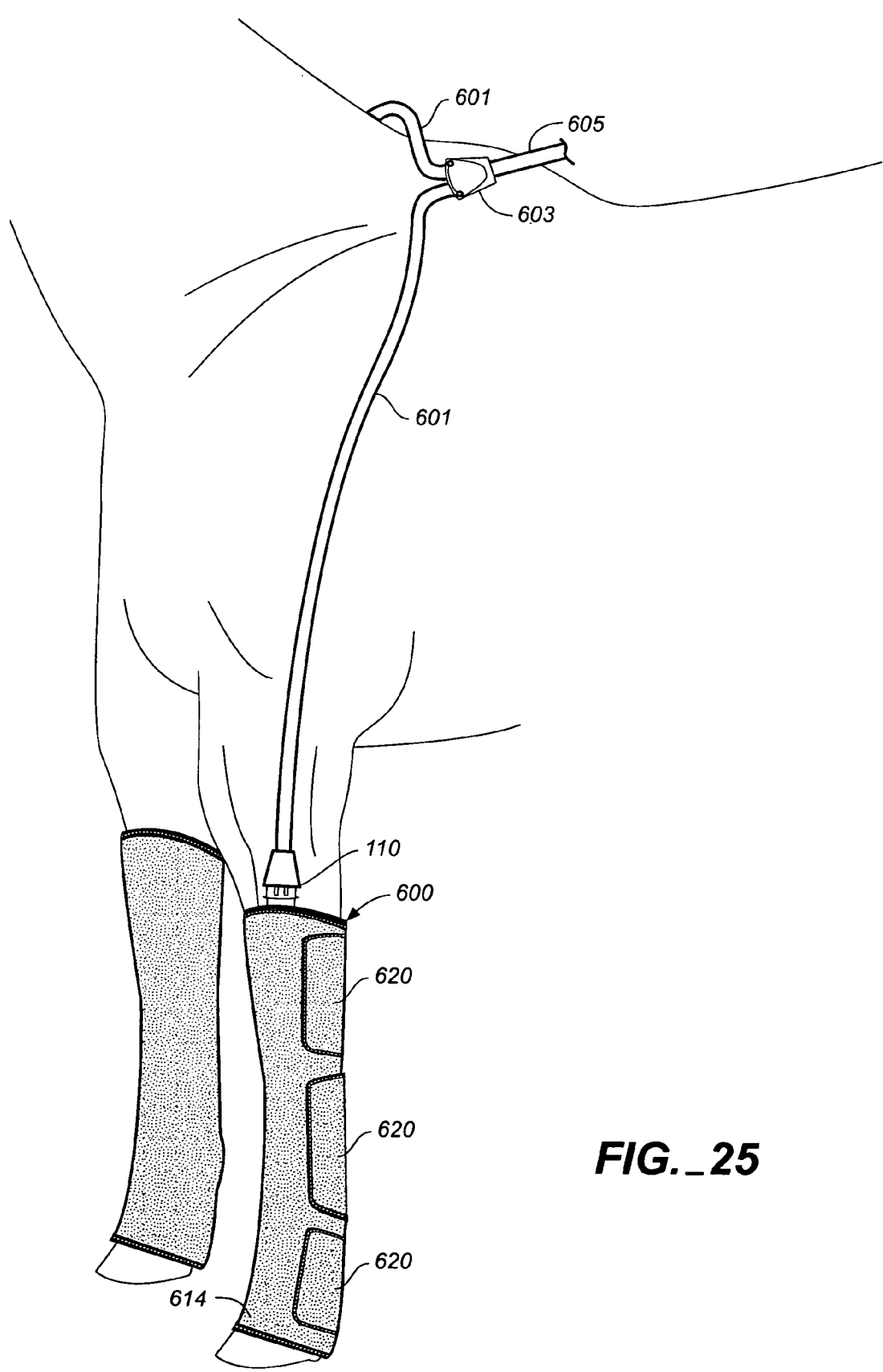
FIG._25

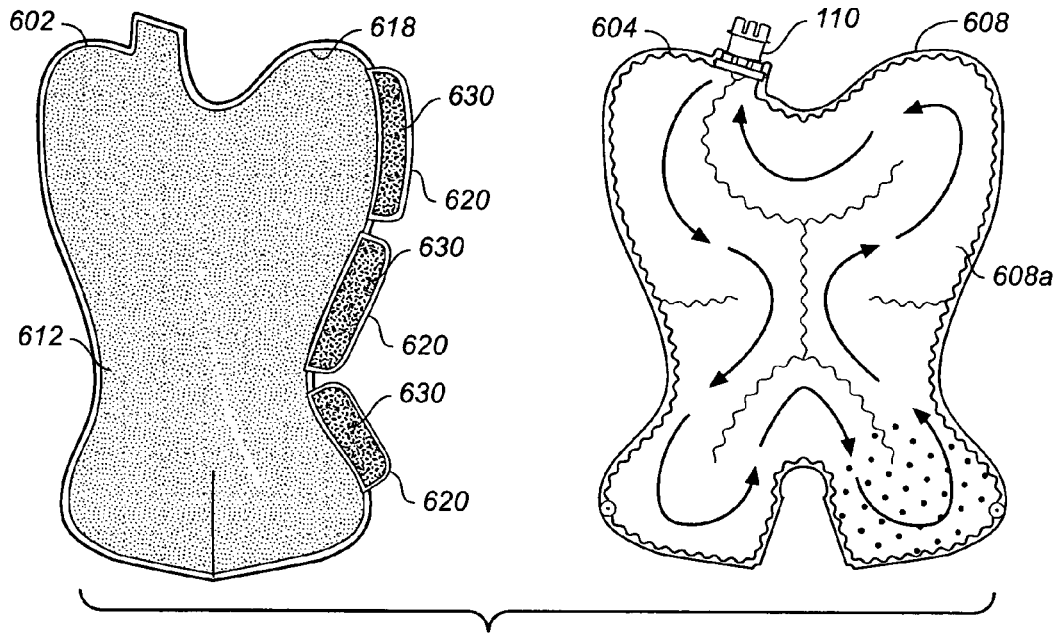
FIG._26
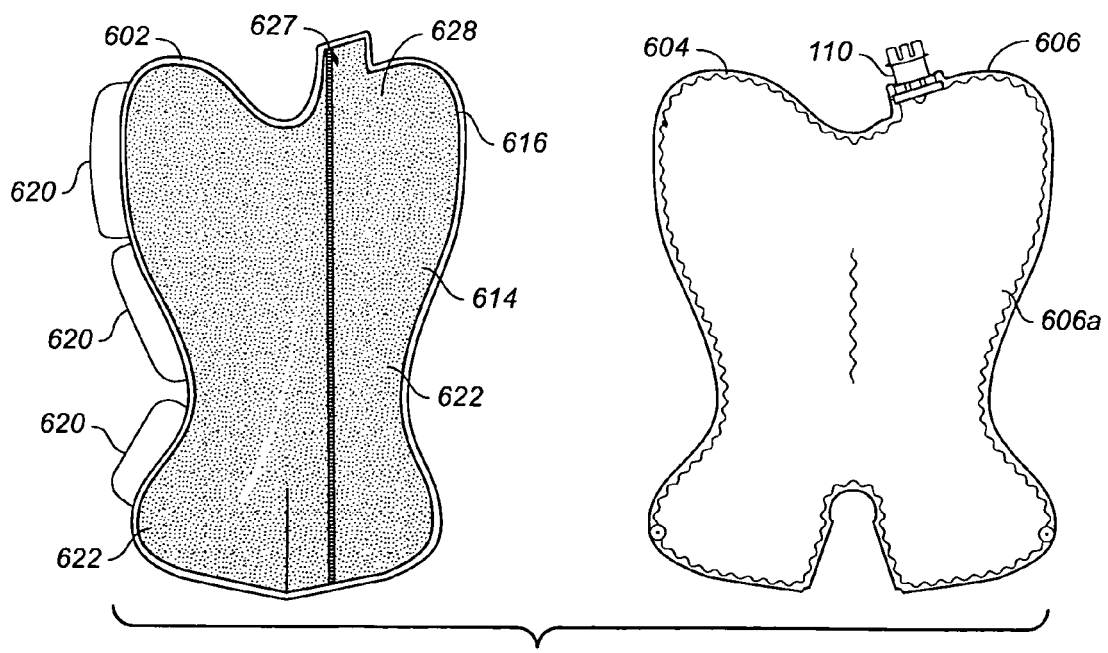
FIG._27

MODULAR APPARATUS FOR THERAPY OF AN ANIMATE BODY

FIELD OF THE INVENTION

The present invention relates to therapy of an animate body, and more particularly to modular heat transfer apparatus for treatment of at least a portion of an animate body.

BACKGROUND OF THE INVENTION

It is now common to apply cold and compression to a traumatized area of a human body to facilitate healing and prevent unwanted consequences of the trauma. In fact, the acronym RICE (Rest, Ice, Compression and Elevation) is now used by many.

Cold packing with ice bags or the like traditionally has been used to provide deep core cooling of a body part. Elastic wraps are often applied to provide compression.

It will be appreciated that these traditional techniques are quite uncontrollable. For example, the temperature of an ice pack will, of course, change when the ice melts, and it has been shown that the application of elastic wraps and, consequently, the pressure provided by the same, varies considerably even when the wrappers are experienced individuals.

Because of these and other difficulties, many in the field have turned to more complicated animate body heat exchanger. Most effective animate body heat exchangers typically include two major components, an external compliant therapy component covering a body part to be subjected to heat exchange, and a control component for producing a flowing heat exchange liquid. Many control units also produce and supply an air or other gas pressure needed to apply pressure to a body part and to press the heat exchange liquid toward such body part. This air pressure is directed to another compliant bladder of the therapy component, which air pressure bladder overlays the liquid bladder to press such liquid bladder against the body part to be subjected to heat exchange, as well as apply compression to the body part to reduce edema.

As can be seen, a commonly used external therapy component uses a pair of compliant bladders to contain fluids; that is, it preferably has both a compliant bladder for containing a circulating heat exchange liquid and a gas pressure bladder which overlays the liquid bladder for inhibiting edema and for pressing the liquid bladder against the body part to be subjected to heat exchange. One problem is that in many therapy component configurations of this nature, the gas pressure bladder tends to "balloon" or, in other words, expand to a much greater degree than is desired. This unwanted expansion can be the cause of several problems. For one, it can actually pull away from the body part, some or all of the conformal heat exchange bladder. For another, it can reduce its edema inhibition ability, as well as reduce the desired effect of pressing the heat exchange bladder into contact with the body part.

Commonly used external therapy components use hook and loop fastening systems in order to allow the therapy component to be applied to a wide variety of body sizes and to give skilled users maximum flexibility in application. The hook and loop fastener is commonly a permanent and integral part of the therapy component, and can be attached by a variety of means including but not limited to sewing, RF welding, gluing, and heat sealing. There are several problems with the permanent attachment of a hook and loop fastening system to the therapy component. First, forces may resolve disadvantageously when the hook and loop fastener is secured, which can result in peeling the hook and loop fastener open and decreasing effective compression. Second, a sewn assembly is relatively stiff, resulting in less even distribution of compression therapy, as well as a higher probability of folds in the assembly that can cause fluid flow to be cut off as compression increases. Third, the therapy component is typically in direct contact with the skin, but RF welded soft heat exchangers cannot be machine washed making it more difficult to provide sanitary treatment in clinical settings or in rental situations. Finally, hook and loop fasteners have a limited lifetime and when they wear out, the entire therapy component must be scrapped.

There remains a need to provide efficient heat transfer therapy apparatus and methods.

SUMMARY OF THE INVENTION

The present invention involves improvements in heat transfer therapy apparatus and avoids disadvantages in the prior art.

According to one embodiment of the invention, modular therapy apparatus for treatment of at least a portion of an animate body comprises a first modular member comprising a heat transfer device adapted to transfer heat between the device and the at least a portion of an animate body; and a second modular member forming a pouch having a perimeter and adapted to receive the first modular member, the second modular member comprising a front side and a back side, the front side having a hook portion, which forms the hook portion of a hook and loop fastener, the back side having a loop portion, which forms the loop portion of the hook and loop fastener, whereby the second modular member can be wrapped around the at least a portion of an animate body and the hook and loop portions fastened to one another to secure the second modular member with the first modular member positioned therein to the at least a portion of the animate body. Among the many advantages of the invention is that it can improve effective delivery of therapy.

According to another embodiment of the invention, modular therapy apparatus for treatment of at least a portion of an animate body comprises a first modular member comprising a heat transfer device adapted to transfer heat between the device and at least a portion of the animate body; and a second modular member forming a pouch having a perimeter and adapted to receive the first modular member, the second modular member comprising a front side and a back side, the front side having a hook portion, which forms the hook portion of a hook and loop fastener, the back side having a loop portion, which forms the loop portion of the hook and loop fastener, the loop portion being non-stretch material.

According to another embodiment of the invention, modular therapy apparatus for treatment of an animate body comprises a first modular member comprising a heat transfer device adapted to transfer heat between the device and the animate body, the heat transfer device comprising a first bladder and a second bladder; the first bladder adapted to circulate a coolant and the second bladder being inflatable; and a second modular member forming a pouch having a perimeter and adapted to receive the first modular member, the first and second modular members being removable from one another after the first modular member has been placed in the pouch.

According to another embodiment of the invention, a modular therapy system for treatment of an animate body comprises a first modular member comprising a heat transfer device adapted to transfer heat between the device and the animate body, the heat transfer device comprising a first bladder for circulating coolant and a second bladder that is inflatable; a coolant source fluidly coupled to the first bladder; a gas source fluidly coupled to the second bladder; and a second modular member forming a pouch having a perimeter and adapted to receive the first modular member, the first and second modular members being removable from one another after the first modular member has been placed in said pouch.

According to another embodiment of the invention, a system for treatment of differently sized animate body members comprises a first modular member comprising a heat transfer device; a second modular member forming a pouch having a perimeter and adapted to receive the first modular member, the second modular member comprising a front side and a back side, the front side having a hook portion, which forms the hook portion of a hook and loop fastener, the back side having a loop portion, which forms the loop portion of the hook and loop fastener; and a third modular member forming a pouch adapted to receive the first modular member; the second modular member comprising a front side and a back side, the front side having a hook portion, which forms the hook portion of a hook and loop fastener, the back side having a loop portion, which forms the loop portion of said hook and loop fastener, the third modular member pouch having the same configuration and size as the second modular member pouch and the third modular member being larger than the second modular member.

According to another embodiment of the invention, a method of assembling heat transfer apparatus for an animate body comprises providing a plurality of same sized bladders adapted for carrying heat transfer medium; providing a plurality of differently sized covers each with a pouch, wherein the pouches are of the same size and are adapted to receive a respective one of the bladders; selecting a cover; and inserting one of the bladders in the pouch of the selected cover.

The above is a brief description of some deficiencies in the prior art and advantages of the present invention. Other features, advantages, and embodiments of the invention will be apparent to those skilled in the art from the following description and accompanying drawings, wherein, for purposes of illustration only, specific forms of the invention are set forth in detail.

BRIEF DESCRIPTION OF THE DRAWINGS

FIG. 1 is a perspective view of one embodiment of the invention;

FIG. 2 illustrates top plan views of modular portions of the embodiment of FIG. 1;

FIG. 3 illustrates bottom plan views of the modular portions of FIG. 2;

FIG. 3A is an enlarged section of a portion of one of the modular portions of FIG. 3 illustrating a dot connection pattern;

FIG. 4 illustrates coupling the modular portions of FIG. 2;

FIG. 5A illustrates the modular portions of FIG. 4 with one modular portion enclosed in a pouch in the other or outer modular portion;

FIG. 5B illustrates a variation of FIG. 5A where the inner enclosed portion has the same dimension and the out modular portion, which encloses the inner modular portion, is larger;

FIG. 6 is a sectional view taken along line 6-6 in FIG. 5A;

FIGS. 6A and 6B diagrammatically illustrate the true grain orientation of the heat transfer device layers illustrated in FIG. 6 in accordance with one embodiment of the invention;

FIGS. 7A-C illustrate use of the embodiment of FIG. 1, where FIG. 7A illustrates applying the apparatus to the arm of a human user; FIG. 7B illustrates the apparatus wrapped around the arm; and FIG. 7C illustrates the apparatus wrapped around the lower portion or calf of the user;

FIG. 8 illustrates another embodiment of the invention;

FIGS. 9A-B illustrate use of the embodiment of FIG. 8, where FIG. 9A illustrates the apparatus being wrapped around a human patient's upper leg and knee and FIG. 9B illustrates the apparatus fully wrapped around that region and ready for use;

FIG. 10 illustrates bottom plan views of modular portions of another embodiment of the invention which, for example, is suitable for coupling to the patient's body core region;

FIG. 11 illustrates top plan views of the modular portions of FIG. 10;

FIG. 12 is a sectional view of the embodiment of FIG. 10 with the modular portions coupled;

FIG. 13A illustrates coupling of the modular portions so that one modular portion is enclosed in a pouch in the other or outer modular portion;

FIGS. 13B and 13C show two positions of the embodiment of FIG. 10 after insertion of the one modular portion as shown in FIG. 13A, wherein FIG. 13B shows the belt or strap portions arranged downward and FIG. 13C show the belt or strap portions arranged upward;

FIGS. 14A-D diagrammatically depict use of the embodiment of FIG. 10 where FIG. 14A show a first step in wrapping the apparatus around the waist of a patient, FIG. 14B shows securing the apparatus in place, FIG. 14C shows the apparatus being in its final position and ready for use, and FIG. 14D shows the apparatus with the straps repositioned and the apparatus being wrapped around the upper torso of the patient;

FIG. 15 illustrates another embodiment of the invention, which, for example, can be used to treat the ankle and foot region of a patient;

FIG. 16 illustrates top plan views of modular portions of the embodiment of FIG. 15;

FIG. 17 illustrates bottom views of the modular portions of FIG. 16;

FIGS. 18A-C illustrate coupling the modular portions of the embodiment of FIG. 16. where FIG. 18A illustrates a first stage of inserting one modular portion into the other modular portion, FIG. 18B illustrates another stage of inserting the one modular portion into the other, and FIG. 18C illustrates the one modular portion fully inserted into the other modular portion;

FIGS. 19A-D illustrate use of the embodiment of FIG. 10, where FIG. 19A shows a first stage in wrapping the device; FIG. 19B illustrates securing mating hook and loop fastener portions around the foot; FIG. 19C illustrates securing mating hook and loop fastener portions at the forward portion of the lower leg of the patient, and FIG. 19D illustrates securing mating hook and loop fastener portions behind the ankle and region adjacent thereto;

FIG. 20 illustrates another embodiment of the invention, which, for example, can be used to treat the shoulder of a patient;

FIG. 21 illustrates top views of modular portions of the embodiment of FIG. 20;

FIG. 22 illustrates bottom views of the modular portions of FIG. 21;

FIGS. 23A-D illustrate coupling the modular portions of FIG. 20, where FIG. 23A illustrates a first stage where the modular portions are generally aligned, FIG. 23B illustrate inserting a portion of one modular portion into the other modular portion, FIG. 23C illustrates another stage where the one modular portion is fully positioned in the other, and FIG.

23D illustrates edges or flaps of the covering modular portion secured to enclose the other modular portion; and FIGS. 24A-D diagrammatically illustrate use of the embodiment of FIG. 20 where FIG. 24A shows a first stage in pulling the apparatus over the arm and toward the shoulder of a patient, FIG. 24B illustrates wrapping the apparatus around the shoulder of the patient and securing mating hook and loop fastener portions around the arm; FIG. 24C illustrates securing mating hook and loop fastener portions to secure portions that wrap around the chest of the patient, and FIG. 24D illustrates the apparatus in position for use with an optional strap having one end attached to the apparatus and mating hook and loop fastener portions secured to one another to form a loop for receiving the patient's arm.

FIG. 25 illustrates another embodiment of the invention, which can be used in equine applications;

FIG. 26 illustrates bottom views of modular portions of the embodiment of FIG. 25; and FIG. 27 illustrates top views of the modular portions of FIG. 25.

DETAILED DESCRIPTION OF THE INVENTION

Before the present invention is described, it is to be understood that this invention is not intended to be limited to particular embodiments or examples described, as such may, of course, vary. Further, when referring to the drawings, like numerals indicate like elements.

The invention comprises modular heat transfer therapy apparatus, which includes a first modular member or portion and a second modular member or portion. The first modular member or portion comprises a heat transfer device and the second modular member portion forms a pouch in which the first modular member is placed. The first modular member can be readily removed so that one can clean either or both the first and second modular members and/or replace either of the first and second modular members. For example, the second modular member can be constructed of material so that it is washable and reusable so that the second modular member can be cleaned after being stained with blood or otherwise soiled. This can happen, for example, when there is blood in the area of the portion of the animate body being treated. Alternatively, the second modular member can be made so that it is a low-cost single-user disposable product. The ability to remove the first modular member from the second modular member and clean or replace the latter is especially advantageous when the apparatus is used on different patients. Further, one can replace the first or second modular member when portions thereof are beginning to fail after a long period of use. With this construction, a faulty heat exchanger can be easily replaced. The ability to replace one modular member also can avoid the need to dispose of the entire apparatus, thereby providing the ability to reduce cost over time. The following description, which will readily make apparent many other advantages of the invention, pertains to illustrative examples and is not provided to limit the invention.

Referring to FIG. 1, a perspective view of one embodiment of the invention is shown and generally designated with reference numeral 100. Modular heat transfer therapy apparatus 100 generally comprises first modular member 102 and second modular member 104, which forms a cover for the first modular member and in FIG. 1 is shown in the form of a sleeve. In other words, apparatus 100 is adapted to be wrapped around at least a portion of a patient's body and form a sleeve around that portion.

In FIG. 1, first modular member 102 is inside the second modular member 104 and hidden from view. In the illustrative embodiment, second modular member 104 comprises two compliant bladders, outer bladder 106 (FIG. 2) and inner bladder 108 (FIG. 3), which form separate chambers such as chambers 106a and 108a for different fluids. Compliant bladders 106 and 108 are generally parallel to one another (see FIG. 6) and are made so as to preclude fluid communication therebetween or between chambers 106a and 108a during use. Bladders 106 and 108 can be formed from three sheets of material with one forming a common inner wall for chambers 106a and 108a as will be described in more detail below.

More specifically, outer bladder 106 is adapted to receive a first fluid such as a gas (e.g., air), which can be regulated to provide the desired amount of inflation of the bladder or pressure therein. This inflation or pressure affects the compressive force applied to the animate body during use as will be further described below. Inner bladder 108 is adapted to receive a fluid, such as a coolant, which can be in the form of a cold liquid, to transfer heat away from the animate body part. Alternatively, the fluid supplied to inner bladder 108 can have a temperature higher than ambient so as to heat the animate body part. In the example illustrated in FIG. 1, a three port manifold 110 provides a port for a fluid such as air to be introduced and exhausted from bladder 106 and fluid inlet and outlet ports for circulating fluid through bladder 108. Each port is formed by a tubular member, which has one end adapted to receive a hose connector as is known in the art and another end adapted to be inserted into one of three tubes (not shown) extending form the bladder (described below). Further, each of the manifold fluid inlet and fluid outlet tubular members or passageways can be provided with a valve such as a spring loaded valve that is configured to allow the passage of fluid therethrough when the fluid hose connectors are coupled to the manifold and to prevent fluid flow therethrough when the fluid hose connectors are uncoupled from the manifold as is known in the art. In this manner, fluid such as a liquid coolant is blocked from exiting fluid bladder 108 when the fluid hoses are uncoupled from the manifold. The gas port does not include a valve. As described above, there are three tubes extending from the bladders. One tube extends from bladder 106 and two tubes extend from bladder 108. The tubes extending from bladder 108 can be placed adjacent to the tube extending from bladder 106 with the tube for bladder 106 above and between the tubes for bladder 108. In manufacture, bladder 106 is formed with an opening and bladder 108 is formed with two openings to receive the tubes in the orientation described above. A tube, such as a polyurethane tube, is positioned in each one of these openings and then welded to a respective bladder to form a fluid tight seal therewith. The tubes extending from the bladders typically have an inner diameter of about ⅛ inch. The manifold passageways typically have a diameter of about ¼ inch. Manifold 110 can be inserted into the tubes to form a seal therewith. For example, each manifold tubular member end portion that mates with or is inserted into a respective tube extending from one or the other bladder can be provided with tapered hose barbs to enhance the seal as is well known in the art. A suitable manifold construction is disclosed in U.S. Pat. Nos. 5,104,158 and 5,052,725, both to Meyer, et al. and both entitled Two Piece Female Coupling. The disclosures of U.S. Pat. Nos. 5,104,158 and 5,052,725 are hereby incorporated herein by reference. The manifold, which carries or forms the tubular members, can be configured to mate with the curves of the body when connected to the modular apparatus. It also can be provided with a ridge for finger placement to allow easier removal. A fluid circulation control unit as diagrammatically represented in FIG. 7B and generally designated with reference numeral 180 is coupled to manifold 110 with tubing to fluidly communicate the therapy fluids to bladders 106 and 108 as will be described in more detail below. It should be understood that other manifold configurations and/or couplings to provide fluid flow between the fluid source and the bladders can be used as would be apparent to one of skill in the art. For example, valves need not be provided in the liquid port couplings.

Referring to FIG. 6, further details of one embodiment of the heat transfer or heat exchange device will be described. The illustrative heat transfer or heat exchange device includes compliant bladder 108, which circulates heat exchange fluid or liquid. This bladder is defined by a pair of generally parallel, flexible, or in other words, compliant, and fluid- or liquid-tight, walls or layers of material 152 and 154, which walls are sealed together by, for example, RF welding along their perimeters. Compliant gas pressure bladder 106 which overlays heat exchange bladder 108 as illustrated to direct gas (most simply, air) pressure against the heat exchange bladder 106 to press it towards the portion of the body being treated. This compliant gas pressure bladder 106 is also defined by a pair of generally parallel and flexible walls or layers of material 150 and 152. In this embodiment, wall 152 is a common wall, i.e., one side of the same aids in defining gas pressure bladder 106 whereas the other side aids in defining bladder 108. Thus, three compliant walls or sheets of material are all that is necessary to define the two separate bladders. Wall or layer 150 is also secured to walls 152 and 154 via RF welding along its perimeter.

The connections in the interior of heat exchange liquid bladder 108 include a relatively uniform distribution of dot connections as shown in FIG. 3A and designated with reference character "D." This matrix of connections acts to disperse the liquid throughout the bladder. This dispersion is further aided by curvilinear fence connections provided for the purpose of directing the flow of a liquid. These fence connections are indicated by the reference numeral F in FIG. 3A. In the illustrative embodiment, the dots are formed in a triangular grid.

During the manufacturing process, sheets of material defining the walls 152 and 154 are RF welded together at the dot connections and at the interior fences. At a later time, the wall 150 is RF welded to the other walls at the perimeter of the bladder. This RF welding will also form a common border for walls 150, 152, and 154.

Referring to FIGS. 6A and 6B, the heat transfer or heat exchange device is welded with each of the three layers having a rotated true grain of about 10-30° with respect to one another. This grain rotation can dramatically improve resistance to ripping of the heat exchanger. In the embodiment illustrated in FIG. 6B, sheets 150, 152 and 154 have grain directions indicated with arrows "A," "B" and "C," respectively. Grain direction B of sheet 152 is offset in a counterclockwise direction from grain direction A of sheet 150 by about 30°. And grain direction C of sheet 154 is offset in a clockwise direction from grain direction A of sheet 152 by about 30°.

Each of the walls 150, 152 and 154 can be made of a nylon material suitably coated with polyurethane to provide both the RF welding qualities and the needed liquid or air impermeability. In one embodiment of the invention, the heat transfer or heat exchange device can comprise fabrics (e.g., nylon fabric) that are laminated with asymmetric amounts of polyurethane. That is, the inner surface of the outer wall of the coolant chamber has an extra heavy coating, which corresponds to about a 5 oz coating of polyurethane, while the inner surfaces of the other walls have standard coatings corresponding to about 3 oz coatings of polyurethane. Accordingly, the surfaces of the inner wall of the coolant and air chambers and the inner surface of the outer wall of the air chamber have standard 3 oz coatings. This construction only requires one non-standard fabric (the fabric having the 5 oz coating), while providing the extra polyurethane necessary to produce an extremely robust weld capable of taking or withstanding over 25,000 cycles at 30 psi. This construction can reduce manufacturing costs. It also facilitates using a lighter weight fabric, which can result in a more flexible heat exchanger that can better fit to the body. In another embodiment of the invention, the inner wall of the coolant chamber has a 5 oz coating of polyurethane in order to facilitate a yet stronger bond at the expense of increased manufacturing costs due to the use of a second non-standard fabric. A finish on the nylon material can also provide a permanent antimicrobial finish to prevent mold growth.

Referring to FIGS. 2 and 3, top plan and bottom views of second modular member 104 are shown. Modular member 104 comprises an inner or front side portion 112 and an outer or back side portion 114. Member 104 can be made from various materials and can comprise inner and outer sheets of material that are sewn or fused together. For example, the inner and outer sides can comprise two sheets of fabric, which are sewn together to form seam 116. An additional seam 118 is provided so that seams 116 and 118 form flap or marginal portion 120 and the perimeter of pouch 122, which is adapted to receive first modular member 102. Binding can be provided around the perimeter of second modular member 104 as shown in FIG. 6.

Outer back side portion 114 of second modular member has an opening 124 formed therein for receiving first modular member 102 as shown in FIG. 4. A portion of back side 114, such as portion 126, can be pulled back (FIG. 2) to facilitate positioning the remaining portion of first modular member 102 into the pouch. Numeral 114a indicates the inner surface of back side portion 114 and is shown in the inner surface portion 126. Any suitable fastening means can be used to close opening 124. For example, zipper 127 can be provided along the sides of the opening.

Second modular member 104 also includes a fastener for holding the apparatus in the desired location on the animate body. Accordingly, when the apparatus is wrapped around a portion of or the entire region being treated, the fastener holds the apparatus in place during treatment. In the illustrative embodiment, a hook and loop fastener is used. It should be understood that if the hook and loop fastener wears out, the removable second modular member or sleeve can be readily replaced.

Referring to FIG. 2, the loop material portion 128 of the hook and loop fastener can be integrally formed with or placed over essentially all of outer back side portion 114 of second modular member 104. Alternatively, a strip of loop material can be integrally formed with or placed over a portion or the entire length (measured from the upper to lower edge of member 104 while referring to FIG. 2) of outer back side portion 114 along the side opposite flap 120. The hook material portion of the hook and loop fastener is shown in FIG. 3 and generally designated with reference numeral 130. Hook portion 130 can be in the form of a single strip that extends along the height of inner front side portion 112 (measured from the upper to lower edge, of inner front side portion 112) or it can be integrally formed with front side portion 112 in the same region. It can extend about 50% to 100% of the length of portion 112. Alternatively, hook portion can comprise a plurality of strips, which can be spaced along the length of portion 112.

In the illustrative embodiment, the active areas of the hook and loop fastener are outside the seams forming pouch 122. When compression increases, the forces may tend to resolve as shear forces as compared to other forces that can peel the hook portion from the loop portion.

According to one embodiment, loop portion 128 is non-stretch material. What is meant by non-stretch material or non-stretchable material is material that stretches less than or equal to 3% of its length when held in tension under a load of no more than 10 pounds. The non-stretch loop portion can improve the efficacy of compression on the animate body when the apparatus is in place. Loop portion 128 can be made of non-stretch material, which can be woven or non-woven fabric. Alternatively, loop portion 128 can be made by securing loop material or fabric to non-stretch backing material, which can be woven or non-woven fabric. The non-stretch backing material, for example, can be made of nylon or Tyvek® (strong yarn linear polyethylene). The non-stretch and loop materials can be sewn, fused, or laminated together. Accordingly, outer back side portion 114 can comprise first and second materials where the first material is non-stretch material (e.g., non-stretch woven or non-woven fabric), the second material is loop material and the non-stretch material forms backing for the loop material.

The second modular member 104 or sleeve also can have a permanent antimicrobial finish to prevent mold growth, such as finishes made according to military specification MIL.STD.810D. The finish can be applied by placing the fabric in a chemical dip as is known in the art. The second modular member or sleeve can act as a blood barrier to prevent contamination of the heat exchanger and reduce transmission of bacteria from patient to patient. For example, the inner faces of the second modular member that form the pouch and contact first modular member 102 can be nylon with a durable water repellency (DWR) coating, which is typically a ½ ounce polyurethane coating.

FIG. 5A illustrates the modular portions of FIG. 4 with the first modular member inside second modular member 104 and zipper 127 closing opening 124. In this state, the apparatus is ready to apply to the portion of the body to be treated. Further, the pouch that second modular member 104 forms allows first modular member 102 to float therein. In other words, beyond being confined in pouch 122, there are no connections between first and second modular members 120 and 104. This can provide a more evenly distributed compression around the gas bladder, resulting in improved therapy of the body being treated. Further, since the heat exchange device can move within pouch 122, there is less chance that a portion of the heat exchange device blocks coolant flow when the apparatus is improperly applied to the portion of the body being treated. For example, if an improper fold occurs in the heat exchange device, the heat exchange device may self-correct its position and relieve blockage of coolant flow.

An exemplary use of modular therapy apparatus 100 will be made with reference to FIGS. 7A-C. This example is provided for illustration and is not intended to limit the scope of the invention. Referring to FIG. 7A, apparatus 100 is positioned adjacent to a portion of a human patient's arm to be treated with the apparatus in an open state. Apparatus 100, which is coupled to fluid circulation and pressurizing unit 180, is then wrapped around the patient's arm and the second modular member hook portion 130 along flap 120 fastened to a portion of the loop portion of member 104.

The control unit includes a mechanism for cooling and circulating a liquid coolant, which includes a reservoir for containing ice water. In a practical realization of this embodiment, the liquid is normal tap water. This liquid was cooled by placing ice into the ice box portion of the control unit, resulting in temperatures ranging typically between 40° F. and 50° F. In this connection, the control unit accepts liquid that has been returned from the heat exchange bladder 108. Before reintroducing the heat exchange liquid into bladder 108, it can be mixed with the liquid in the reservoir or it can be directed to bypass the reservoir. That is, the control unit is capable of supplying liquid at other controlled temperatures by means of mixing liquid chilled in the ice box and liquid warmed in the bladder by means of contact with an animate body and returning the mixed liquid to the bladder. The pressure of air furnished by the control unit is generally about 0.25 to 1.5 psig.

It should be noted that the invention is applicable to many other types of therapy components, and the particular liquid, its temperature and pressure will be dependent upon the design and purpose of such therapy components. This is also true of the air pressure and in some instances it is cycled between two pressures (typically between 1.5 and 0.25 psig). Similarly, the second modular member can have various shapes to accommodate different areas of an animate body. Typically, the area of one side of the second modular member will range from about 1 to 6 square ft. In the case of the knee application, this area will be about 6 square ft. In the case of an elbow, this area will be about 1 to 1.5 square ft.

Although apparatus 100 has been described with a dual bladder heat exchange device, a single bladder heat exchange device can be used. In the single bladder embodiment, the bladder is adapted circulate liquid or coolant.

FIG. 5B illustrates one variation of FIG. 5A. The embodiment of FIG. 5B, is the same at that shown in FIG. 5A with the exception that second modular member is modified (as indicated with reference numeral 104') so that the portion of the second modular member outside and to the left side of pouch 122 is larger. That portion is indicated with reference numeral 121 and typically will have a width of at least 1 inch a more specifically in the range of range of 1 to 12 inches. A further seam 118' also can be provided. The ability to enlarge the overall dimension of the second modular member, while maintaining the configuration and dimension of pouch 122 unchanged facilitates using a single heat exchange device with many differently sized second modular members or sleeves to treat differently sized patients or different body portions. Accordingly, another embodiment of the invention comprises a system for treatment of differently sized members. The system includes a plurality of differently sized second modular members each having a pouch 122 of the same configuration and size and a plurality of first modular members 102, each adapted to fit in any of the pouches or each being of the same size and configuration. The second modular member can be selected based on the animate body portion being treated and combined with any one of the heat exchange devices.

Referring to FIG. 8, another embodiment of the invention is shown and generally designated with reference numeral 200. Modular therapy apparatus 200 is the same as apparatus 100 with the exception that it is larger and its configuration is slightly modified so that it better adapted to from a sleeve around ones upper leg and knee as shown in FIGS. 9A and 9B. Accordingly flap 220, which includes a hook portion that is hidden from view, is the same as flap 120 with the exception that it is larger and its configuration is slightly modified as shown in the drawings.

Referring to FIGS. 10 and 11, another embodiment of the invention is shown and generally designated with reference numeral 300. As will be described in more detail below, apparatus 300 can be used, for example, to treat the core or torso of a human body. FIG. 10 illustrates bottom plan views of the modular portions of apparatus 300 and FIG. 11 illustrates top plan views of the modular portions of FIG. 10.

Apparatus 300 comprises first modular member 302 and second modular member 304. First modular member 302 includes gas bladder 306 and fluid or coolant bladder 308. Bladders 306 and 308 form chambers 306a and 308a, respectively. Except for the configuration of first modular member 302, first modular member 302 is the same as first modular member 102 and can be made in the same manner, with the exception that a plurality of connections between the walls defining the modular member or air bladder 302 can be provided.

More specifically, and with reference to FIG. 12, which a sectional view of apparatus 300, a plurality of connections between the walls defining modular member or air bladder 302 can be provided as described in U.S. Pat. No. 6,695,872 to Elkins, the disclosure of which is hereby incorporated herein by reference. Such connections can minimize or eliminate undesirable ballooning when the bladder is pressurized. In the illustrative embodiment, in which the bladders are formed by RF welding (see e.g., FIG. 12), this is simply achieved by forming some of the connections normally provided in liquid bladder 308, while sheet 350 is in place as will be described in more detail below. The result is that these connections are also formed in air bladder 306, that is, these connections are both within the liquid bladder and in the air bladder. It appears functionally as if the desired connections provided in the liquid bladder are "telegraphed" also to appear in the air bladder. These connections in the two bladders, of course, register with one another.

In the illustrative embodiment, the shape of gas pressure bladder 306 conforms to the shape of the heat exchange bladder 308. Fences or dividers in the heat exchange bladder to direct fluid flow can be also provided in the gas pressure bladder. These control fences are indicated by the reference numeral C in FIG. 12. They can be provided in bladder 306 not only for the purpose of directing the flow of a liquid or gas, but also to secure the walls defining the gas pressure bladder together at various locations within the interior of such bladder. These connections provided by the fences C can prevent the gas bladder from "ballooning" out as described above and causing the temperature control liquid bladder not to conform to the body part. These fences register with the comparable fences in the liquid bladder.

During the manufacturing process, sheets of material defining the walls 352 and 354 are RF welded together at the dot connections and if desired, at the interior fences. At a later time the wall 350 is RF welded to the other walls at the perimeter of the bladder with any interior fences being formed as needed. Such fences C will thereby be formed in both bladders providing the desired liquid flow directors in the liquid bladder and the connections in the air bladder. This RF welding will also form a common border for walls 350, 352, and 354.

The inner fences construction also can be provided in the gas bladder of the embodiment of FIGS. 20-24, which is described in detail below.

Second modular member 304 is the same as second modular member 104 with the exception that second modular member is differently configured and includes central portion 304a, and straps or strap portions 304b and 304c. Strap portions 304b and 304c are secured to central portion 304a as will be described in more detail below. Second modular member central portion 304a comprises an inner or front side portion 312 and an outer or back side portion 314. Central portion 304a can be made from various materials and can comprise inner and outer sheets of material that are sewn or fused together as previously described in connection with member 104 and can include seam 316 which defines the perimeter of pouch 322. Pouch 322 is adapted to receive first modular member 302. Strap portions 304b and 304c can comprise one or more layers of material. When more than one layer is used, the layers can be sewn or fused together as would be apparent to one skilled in the art.

Outer back side portion 314 of central portion 304a has an opening 324 formed therein for receiving first modular member 302 as shown in FIG. 13A. Any suitable fastening means can be used to close opening 124. For example, zipper 327 can be provided along the sides of the opening (FIGS. 13B & C).

Second modular member 304 also includes a fastener for holding the apparatus in the desired location on the animate body. Accordingly, when the apparatus is wrapped around a portion of or the entire region being treated, the fastener holds the apparatus in place during treatment. As in the embodiments described above, a hook and loop fastener is be used in this illustrative embodiment.

Referring to FIG. 11, the loop material portion 328 of the hook and loop fastener can be integrally formed with or placed over essentially all of outer back side portion 314 of second modular member 304. Therefore, the loop material portion can cover the outer back side surface of center portion 304a, and strap portions 304b and 304c (FIG. 11). Alternatively, a strip of loop material can be integrally formed with or placed over a portion or the entire length (measured from the upper to lower edge of member 304) adjacent the outer end of portion 304c and along interface with center portion 304a. According to one embodiment, loop portion 328 is non-stretch material and can be made in the same manner as loop portion 128 as described above.

The hook material portion of the hook and loop fastener that fastens the apparatus to the animate body is shown in FIG. 10 and generally designated with reference numeral 330. Hook portion 330 is positioned on the front side portion 312 of strap 304b and can be in the form of a single strip that extends along the outer end portion of strap 304b or it can be integrally formed with the front side portion of 304b. It can extend about 50% to 100% of the length of strap 304b. Alternatively, hook portion can comprise a plurality of strips, which can be spaced from one another. Hook material portions 330 also are provided along the inner end portions of straps 304b and 304c. These portions are shown in dashed line in FIG. 10.

In the illustrative embodiment, the active areas of the hook and loop fastener on the outer end portions straps 304b and 304c are outside the seam forming pouch 122. When compression increases, the forces may tend to resolve as shear forces as compared to other forces that can peel the hook portion from the loop portion. The hook and loop fastener that operates between the inner end portions of strap portions 304b and 304c and center portion 304a facilitate removal of the strap portions. This, in turn, facilitates replacement of either or both straps or repositioning of the straps. For example, the straps can be portioned as shown in FIG. 13B, which may be preferred when treating the upper torso of a patient. Alternatively, the straps can be removed and repositioned as shown in FIG. 13C, which may be preferred when treating the lower portion of the patient's torso.

FIGS. 14A-D diagrammatically depict use of the apparatus 300 where FIG. 14A show a first step in wrapping the apparatus around the waist or lower portion of the torso of a patient, FIG. 14B shows securing the apparatus in place, and FIG. 14C shows the apparatus being in its final position and ready for use. FIG. 14D shows the apparatus with the straps repositioned and the apparatus being wrapped around the upper torso of the patient.

Referring to FIG. 15, another embodiment of the invention is shown and generally designated with reference numeral 400. Modular therapy apparatus 400 can be used, for example, to treat an ankle and/or foot of a patient. FIG. 16 illustrates top plan views of modular portions of apparatus 400 and FIG. 17 illustrates bottom views of the modular portions of apparatus 400.

Apparatus 400 comprises first modular member 402 and second modular member 404. First modular member 402 includes gas bladder 406 and fluid or coolant bladder 408. Bladders 406 and 408 form chambers 406a and 408a, respectively. Except for the configuration of first modular member 402, first modular member 402 is the same as first modular member 102 and can be made in the same manner.

Second modular member 404 is the same as second modular member 104 with the exception that second modular member is differently configured, has differently positioned hook portions and has heel alignment marker 405. Accordingly, member 404 can be made from various materials and can comprise inner and outer sheets of material that are sewn or fused together as previously described in connection with member 104 and can include seam 416, which in combination with seams 418, defines the perimeter of pouch 422. Pouch 422 is adapted to receive first modular member 402.

Outer back side portion 414 has an opening 424 formed therein for receiving first modular member 402 as shown in FIG. 16. Zipper 427 can be provided along the sides of the opening (FIG. 18C).

Second modular member 404 also includes a fastener for holding the apparatus in the desired location on the animate body and can include the hook and loop fastener system described in connection with apparatus 100. Referring to FIG. 11, the loop material portion 428 of the hook and loop fastener can be integrally formed with or placed over essentially all of outer back side portion 414 of second modular member 404. Alternatively, a strip of loop material can be integrally formed with or placed over a portion of back side portion 414 that would cooperate with the hook portions in accordance with FIGS. 17 and 19A-C. According to one embodiment, loop portion 428 is non-stretch material and can be made in the same manner as loop portion 128 as described above.

The hook material portion of the hook and loop fastener that fastens the apparatus to the animate body is shown in FIG. 17 and generally designated with reference numeral 430. Hook portions 430 can have a width of about 4 inches. In the illustrative embodiment, the active areas of the hook and loop fastener are outside the seams forming pouch 422, which can provide similar advantages to those described above regarding force resolution when the apparatus is under compression.

FIGS. 18A-C illustrate inserting the modular member 402 into modular member 404. where FIG. 18A illustrates a first stage of inserting modular member 402 into modular member 404. FIG. 18B illustrates another stage portion into the other and FIG. 18C illustrates member 402 fully inserted and zipper 327 closed.

FIGS. 19A-D illustrate use of the embodiment of FIG. 10. First one places one's foot on inner side portion 412 with one's heel aligned along U-shaped marker 405. Flap V is wrapped over the foot and flap W secured thereto with hook portion 430 FIGS. 19A & B). Flap X is wrapped around the ankle and leg and then flap Y is wrapped thereover and secured thereto with hook portion 430 (FIG. 19C). Flap Z is then wrapped around the leg and over flap Y and secured thereto with hook portion 430 (FIG. 19D).

Referring to FIG. 20, another embodiment of the invention is shown and generally designated with reference numeral 500. Apparatus 500 can be used to treat the shoulder of a patient. FIG. 21 illustrates top views of the modular members of the apparatus 500 and FIG. 22 illustrates bottom views of the modular members shown in FIG. 21.

Apparatus 500 comprises first modular member 502 and second modular member 504. First modular member 502 includes gas bladder 506 and fluid or coolant bladder 508. Bladders 506 and 508 form chambers 506a and 508a, respectively.

First modular member 502 is the same as first modular member 102 except for the configuration of modular member 502, including flap portions 562, and that it can include the inner fence construction described above in connection with the embodiment of FIGS. 10-14. Modular member 502 also differs from modular member 102 in that it includes a coupling mechanism for coupling these flap portions. More specifically, flap portions 562 are coupled to one another through elastic cord 560, which is laced through holes formed in first modular member 502. The elastic cord substantially maintains flaps 562 in the closed position shown in FIG. 21 when bladder 506 is inflated and fluid circulated through bladder 508.

Second modular member 504 is the same as second modular member 104 with the exception that second modular member is differently configured and includes central portion 504a, and straps or strap portions 504b, 504c, and 504d. Strap portions 504b, c & d are secured to central portion 504a as will be described in more detail below. Second modular member central portion 504a comprises an inner or front side portion 512 and an outer or back side portion 514. The arm sling 540 can be coupled to second modular member 504 through a plurality of snap connectors "S" or any other suitable connector including but not limited to hook and loop fasteners. Central portion 504a can be made from various materials and can comprise inner and outer sheets of material that are sewn or fused together as previously described in connection with member 104 and can include seam 516, which in combination seam 518, define the perimeter of pouch 522. Pouch 522 is adapted to receive first modular member 502. Strap portions 504b, c, and d can comprise one or more layers of material. When more than one layer is used, the layers can be sewn or fused together as would be apparent to one skilled in the art.

Outer back side portion 514 has an opening 524 formed therein for receiving first modular member 502 as shown in FIG. 16. Zipper 527 can be provided along the sides of the opening (FIG. 18C).

Second modular member 504 also includes a fastener for holding the apparatus in the desired location on the animate body and can include the hook and loop fastener system described in connection with apparatus 100. Referring to FIG. 21, the loop material portion 528 of the hook and loop fastener can be integrally formed with or placed over essentially all of outer back side portion 514 of second modular member 504. Alternatively, a strip of loop material can be integrally formed with or placed over a portion of back side portion 514 that would cooperate with the hook portions described below. According to one embodiment, loop portion 528 is non-stretch material and can be made in the same manner as loop portion 128 as described above.

The hook material portion of the hook and loop fastener that fastens the apparatus to the animate body and generally designated with reference numeral 530. The hook portion of strap portion 504b can comprise two sections, each having a length extending along the length of the strap of about 4 or 5 inches. These sections can be spaced apart by about 1 inch to facilitate or improve flexibility of the end portion of the strap. In this manner, the strap can be readily folded to provide length adjustment for differently sized users. In the illustrative embodiment, the active areas of the hook portion of the hook and loop fastener are outside the seams forming pouch 522, which can provide similar advantages to those described above regarding force resolution when the apparatus is under compression.

FIGS. 23A-D illustrate coupling the modular members 502 and 504 where FIG. 23A illustrates aligning modular member 502 with opening 524 in second modular member outer back side portion 514. FIGS. 23B and C show insertion of modular member 502 into modular member 504 and FIG. 24D shows back side portion 514 closed and zipped up.

FIGS. 24A-D diagrammatically illustrate use of apparatus 500 where FIG. 24A shows a first stage in pulling the apparatus over the patient's arm and toward the patient's shoulder. FIG. 24B illustrates positioning the apparatus over the shoulder of the patient and securing hook portions of straps 504c and 504d to portions of central portion 504a which are constructed with loop material to secure apparatus 500 to the patient's arm. Strap 504b is then pulled under the patient's other shoulder and a portion of its hook portion is ready to be fastened to the loop material of central portion 504a (FIG. 24C). In FIG. 24C, the end portion of strap 504b is folded back along the space between hook portions 530 and secured in that position by tucking into a pocket designed to accept it. This facilitates shortening the strap for smaller patients. The end portion of strap 504b can be unfolded to extend the length of the strap for larger patients as shown in FIG. 24D. FIG. 24D also shows optional strap 640, which can be used to hold up the lower arm of the patient. Strap 540 can have a hook portion on one end and snaps at the opposite end so that the hook portion can be fastened to loop material the outer side portion 514 or second modular member 504 and the snaps can be fastened to the snaps on modular portion 504.

Referring to FIG. 25, a further embodiment of the invention is shown and generally designated with reference numeral 600. Apparatus 600 is especially suited for equine applications. In FIG. 25, apparatus 600 is shown wrapped around at horse's leg. The therapy fluids are delivered though the hose 601, which has one end coupled to apparatus 600 through manifold 110 and its other end coupled to a therapy fluid circulation control unit such as control unit 160. Accordingly, conduit 601 can have three channels for fluid flow (e.g., two for liquid or gas coolant and one for gas). When a single apparatus is used, conduit 601 is directly fluidly coupled to a fluid circulation control unit. However, when it is desired to treat two legs, a Y-connector can be provided as shown in FIG. 25. One such Y-connector is diagrammatically shown and indicated with reference numeral 603. In this case, another conduit such as conduit 605 fluidly couples the Y-connector 603 with the circulation control unit (not shown). The Y-connector facilitates fluidly coupling each conduit 601, which is fluidly coupled to a respective apparatus 600 through a manifold 110, to the circulation control unit so that a plurality of legs (i.e., 2) can be treated at the same time.

FIG. 26 illustrates bottom plan views of modular portions of apparatus 600 and FIG. 17 illustrates top views of the modular portions of apparatus 600. Apparatus 600 comprises first modular member 602 and second modular member 604. First modular member 602 includes gas bladder 606 and fluid or coolant bladder 608. Bladders 606 and 608 form chambers 606a and 608a, respectively. Except for the configuration of first modular member 602, first modular member 602 is the same as first modular member 102 and can be made in the same manner.

Second modular member 604 is the same as second modular member 104 with the exception that second modular member is differently configured including differently configured hook portions 630. Accordingly, member 604 can be made from various materials and can comprise inner and outer sheets of material that are sewn or fused together as previously described in connection with member 104 and can include seam 616, which defines the perimeter of pouch 622. Pouch 622 is adapted to receive first modular member 602. Inner side portion 612 is placed against the portion of the body being treated and outer back side portion 614 has an opening formed therein for receiving first modular member 602. The opening is shown closed with zipper 627 in FIG. 27.

Second modular member 604 also includes a fastener for holding the apparatus in the desired location on the animate body and can include the hook and loop fastener system described in connection with apparatus 100. Referring to FIG. 27, the loop material portion 628 of the hook and loop fastener can be integrally formed with or placed over essentially all of outer back side portion 614 of second modular member 604. Alternatively, it can be integrally formed with or placed over the right portion of zipper 627 or the side of zipper 627 opposite flaps 620. According to one embodiment, loop portion 628 is non-stretch material and can be made in the same manner as loop portion 128 as described above.

The hook material portion(s) of the hook and loop fastener that fastens the apparatus to the animate body is shown in FIG. 26 and generally designated with reference numeral 630. Hook portions are integrally formed with or secured to flaps 620, which extend outward form seam 618. Hook portions 630 are can have a width of about 3 inches and a length of about 12 to 30 inches.

Regarding manufacture, it can be specialized to make the first modular member, second modular member and any desired configuration thereof. Further, a plurality of any of apparatus 200, 300, 400, 500, and 600 can be provided with differently sized second modular members, but with same sized pouches and same sized first modular members to facilitate component interchangeability in a manner similar to that described in connection with FIG. 5B.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

What is claimed is:

1. Modular therapy apparatus for treatment of an animate body comprising:
   a first modular member comprising a heat transfer device adapted to transfer heat between said device and said animate body, said heat transfer device comprising a first bladder and a second bladder; said first bladder adapted to circulate a coolant and said second bladder being inflatable; and
   a second modular member forming a pouch having a perimeter and adapted to receive said first modular member, said first and second modular members being removable from one another after said first modular member has been placed in said pouch;

wherein said second modular member pouch includes at least two regions and an opening between said at least two regions, said second modular member further including a fastener for fastening said opening closed.

2. The apparatus of claim 1 wherein said first and second bladders form separate chambers.

3. The apparatus of claim 1 wherein said first bladder includes an inlet port and an outlet port and said second bladder includes a port.

4. The apparatus of claim 1 wherein said second modular member comprises a front side and a back side, said front side having a hook portion, which forms the hook portion of a hook and loop fastener, said back side having a loop portion, which forms the loop portion of said hook and loop fastener, said loop portion being non-stretch material.

5. A modular therapy system for treatment of an animate body comprising:
   a first modular member comprising a heat transfer device adapted to transfer heat between said device and said animate body, said heat transfer device comprising a first bladder for circulating coolant and a second bladder that is inflatable;
   a coolant source fluidly coupled to said first bladder;
   a gas source fluidly coupled to said second bladder; and
   a second modular member forming a pouch having a perimeter and adapted to receive said first modular member, said first and second modular members being removable from one another after said first modular member has been placed in said pouch;
   wherein said second modular member pouch includes at least two regions and an opening between said at least two regions, said second modular member further including a fastener for fastening said opening closed.

6. The system of claim 5 wherein said second modular member comprises a front side and a back side, said front side having a hook portion, which forms the hook portion of a hook and loop fastener, said back side having a loop portion, which forms the loop portion of said hook and loop fastener, said loop portion being non-stretch material.

7. A heat transfer apparatus comprising:
   a first bladder comprising:
      a fluid chamber adapted to transfer heat between the apparatus and an animate body by circulating a coolant through the chamber;
   an inlet port; and
   an outlet port; and
   a second bladder comprising:
   an inflatable chamber; and
   an inflation port;
      wherein the inlet port, outlet port, and inflation port comprise a three-port manifold wherein the inlet port, outlet port and inflation port each contain a tube, such that the tubes in the inlet and outlet ports are adjacent to the tube in the inflation port, with the inflation tube above and between the tubes in the inlet and outlet ports.

8. A heat transfer apparatus comprising:
   a first bladder comprising:
      a fluid chamber adapted to transfer heat between the apparatus and an animate body by circulating a coolant through the chamber;
   an inlet port; and
   an outlet port; and
   a second bladder comprising:
   an inflatable chamber; and
   an inflation port;
wherein the inlet port, outlet port, and inflation port comprise a three-port manifold
   wherein the tubes are sealed with the first and second bladders to form a fluid-tight seal therewith.

* * * * *